United States Patent [19]

Shenvi et al.

[11] Patent Number: 4,499,082
[45] Date of Patent: Feb. 12, 1985

[54] α-AMINOBORONIC ACID PEPTIDES

[75] Inventors: Ashokkumar B. Shenvi; Charles A. Kettner, both of Wilmington, Del.

[73] Assignee: E. I. Du Pont de Nemours and Company, Wilmington, Del.

[21] Appl. No.: 558,362

[22] Filed: Dec. 5, 1983

[51] Int. Cl.³ .................... A61K 37/00; A61K 31/44; C07C 103/52
[52] U.S. Cl. ................ 514/2; 260/112.5 R; 514/18; 514/19
[58] Field of Search ............. 424/263, 177; 260/112.5 R

[56] References Cited

U.S. PATENT DOCUMENTS 4,369,183  1/1983  Jones ................... 424/263

FOREIGN PATENT DOCUMENTS 2040291A  8/1980  United Kingdom .

OTHER PUBLICATIONS

Leinhard, *Enzyme Inhibitors as Drugs*, Sandler, Ed., (University Park Press, Baltimore, 1980), pp. 43–51.
Koehler et al., *Biochemistry* $10$:2477 (1971).
Matteson et al., *J. Am. Chem. Soc.* $103$:5241 (1981).
Lindquist et al., *Arch. Biochem. Biophys.* $160$:135 (1974).
Lindquist et al., *J. Am. Chem. Soc.* $99$:6435 (1977).
Powers et al., *Biochim. Biophys. Acta.* $485$:156 (1977).
Kleinerman et al., *Am. Rev. Resp. Dis.* $121$:381 (1980).
Janoff et al., *Am. Rev. Resp. Dis.* $121$:1025 (1980).
Stone et al., *Am. Rev. Resp. Dis.* $124$:56 (1981).
Powers et al., *Biochem. Biophys, Res. Comm.* $67$:639 (1975).
Lestienne et al., *J. Biol. Chem.* $254$:5219 (1979).
Teshima et al., *J. Biol. Chem.* $257$:5085 (1982).
Yoshimura et al., *J. Biol. Chem.* $257$:5077 (1982).
U.S. Patent Application Serial No. 558,361.

*Primary Examiner*—Delbert R. Phillips
*Attorney, Agent, or Firm*—Scott G. Hallquist

[57] ABSTRACT

Peptides comprising C-terminal α-aminoboronic acid residues are potent, reversible inhibitors of proteolytic enzymes.

19 Claims, 3 Drawing Figures

α-AMINOBORONIC ACID PEPTIDES

BACKGROUND OF THE INVENTION

This invention relates generally to enzyme inhibitors, and particularly to a new class of peptide inhibitors of proteolytic enzymes.

Proteases are enzymes which cleave proteins at single, specific peptide bonds. Cuypers, et al., J. Biol Chem. 257:7086 (1982), and the references cited therein, classify proteases on a mechanistic basis into four classes: serine, cysteinyl or thiol, acid or aspartyl, and metalloproteases. Members of each class catalyze the hydrolysis of peptide bonds by a similar mechanism, have similar active site amino acid residues, and are susceptible to class-specific inhibitors. For example, all serine proteases that have been characterized have an active site serine residue, and are susceptible to inhibition by organofluorophosphates and substrate-derived chloromethyl ketones. Metalloproteases are inhibited by chelating agents. The reactivity of more specialized inhibitors with individual proteases is, however, highly dependent upon the structure of the inhibitor, and, in the case of peptide inhibitors, upon amino acid sequence.

Lienhard, in Enzyme Inhibitors as Drugs, Sandler, ed., (University Park Press, Baltimore, 1980) pp. 43–51, suggests that boronic acid analogous (I) of certain amino acids and peptides are likely transition-state analogues, and potentially "extremely potent inhibitors" of serine and thiol proteases.

$$\underset{R_1NHCHCONHCH-B}{\overset{R_2\quad R_3}{|\quad |}}\diagdown_{OH}^{OH} \qquad I$$

Koehler, et al., Biochemistry 10:2477 (1971), disclose inhibition of chymotrypsin, a serine protease, by 2-phenylethaneboronic acid ($K_i$=2.9 mM). Matteson, et al., J. Am. Chem. Soc. 103:5241 (1981) describe preparation of (R)-1-acetamido-2-phenylethaneboronic acid (II) and its use as an inhibitor of chymotrypsin ($K_i$=4 μM).

Lindquist, et al., Arch. Biochem. Biophys. 160:135 (1974), describe use of 2-phenylethaneboranic acid and benzeneboronic acid as inhibitors of subtilisin, a bacterial chymotrypsin-like serine protease. Lindquist, et al., J. Am. Chem. Soc. 99: 6435 (1977), disclose synthesis of N-benzoylaminomethaneboronic acid, and use of the latter compound as a potent, competitive inhibitor of α-chymotrypsin ($K_i$=1–4 μM). However, Matteson, et al., J. Am. Chem. Soc. 103:5241 (1981) suggest that the compound actually obtained by Lindquist, et al., was more likely an isomer, the imido ester III.

Aberrant proteolysis has been associated with disease states in man and experimental animals, notably emphysema. Barrett, in Enzyme Inhibitors as Drugs, Sandler, ed., (University Park Press, Baltimore, 1980) pp. 216–229, and the references cited therein, suggests possible contributory roles for the human neutrophil serine proteases, elastase and cathepsin G, in a diverse group of disease states marked by proteolysis and consequent tissue destruction. Included are rheumatoid arthritis, corneal ulcers, and glomerular nephritis. Further, the tissue damage resulting from bacterial and other parasitic infections may be attributable to the activity of serine proteases of pathogenic origin.

Emphysema is defined by the American Thoracic Society as "an anatomic alteration of the lung characterized by an abnormal enlargement of the air spaces distal to the terminal nonrespiratory bronchiole, accompanied by destructive changes of the alveolar walls." In all forms of emphysema the elastic fibers of alveolar walls are disrupted. Considerable evidence has been accumulated for the role of proteolysis in disruption of elastin fibers. Furthermore, this aberrant proteolysis has been ascribed to a leukocyte serine protease, neutrophil elastase. Neutrophil elastase is readily accessible to lung tissue, since neutrophils are sequestered in lung capillaries and connective tissue in response to lung irritants.

Janoff, in Molecular Basis of Biological Processes, Berlin, et al., eds., (Academic Press, New York, 1978) pp. 225–259, reviews evidence for the role of neutrophil elastase in pathogenesis of emphysema. Emphysema can be induced in experimental animals by intrapulmonary administration of certain proteases. The severity of the disease is directly correlated with the elastolytic titer of the protease mixture instilled, while enzymes which do not hydrolyze elastin are ineffective. Laurell, et al., Scand. J. Clin. Lab. Invest., 15:132, (1963), and Tobin, et al., Br. J. Dis. Chest 77:14 (1983), correlate α1-antitrypsin (α1-protease inhibitor) deficiency with incidence of emphysema. Further, Thompson, TIBS 7:349 (1982), reports that 40% of individuals deficient in α1-antitrypsin die of lung disease. α1-Antitrypsin is a major protease inhibitor in plasma, and effectively inhibits neutrophil elastase, exhibiting a $K_{assoc.}$ of $6.5\times10^7 M^{-1}s^{-1}$.

In a continuing search for therapeutic agents useful for treatment of emphysema, several groups have prepared and tested inhibitors of neutrophil elastase. Powers, et al., Biochim. Biophys. Acta 485:156 (1977), tested a number of chloromethyl ketone peptide analogues for inhibitory capacity. Of the compounds tested, N-methoxysuccinyl-L-alanyl-L-alanyl-L-prolyl-L-valine chloromethyl ketone (MeOSuc-Ala-Ala-Pro-ValCH2Cl) was the most effective inhibitor of neutrophil elastase, exhibiting inhibitory activity at a concentration of 25 μM. A related peptidyl chloromethyl ketone, N-acetyl-L-alanyl-L-alanyl-L-prolyl-L-alanine chloromethyl ketone (Ac-Ala-Ala-Pro-AlaCH2Cl) was reported by Kleinerman, et al., Am Rev. Resp. Dis. 121:381 (1980) to effectively block experimentally-induced emphysema in hamsters when administered intraperitoneally. MeOSuc-Ala-Ala-Pro-ValCH2Cl was determined by Janoff, et al., Am Rev. Resp. Dis 121:1025 (1980) to be an effective agent in the treatment of emphysema in mice when given orally. N-succinyl-L-alanyl-L-alanyl-L-prolyl-L-valine chloromethyl ketone (Suc-Ala-Ala-Pro-ValCH₂Cl) was effective in hamsters following intratracheal administration, according to Stone, et al., Am. Rev. Resp. Dis. 124:567 (1981). However, as Janoff, et al., supra, note, many questions regarding the toxicity, immunogenicity, and carcinogenicity of chloromethyl ketones, which are alkylating agents, remain unresolved. Furthermore, the rapid loss of effectiveness of this class of compounds following administration complicates their use as therapeutic agents. For example, the most effective inhibitor tested by Janoff, MeOSuc-Ala-Ala-Pro-ValCH₂Cl, was ineffective if administered to mice more than fifteen minutes prior to challenge by intrapulmonary instillation of elastase.

Other inhibitors of elastase which are reported in the chemical and medical literature include certain aza peptides, disclosed by Powers, et al., Biochem. Biophys. Res. Comm. 67:639 (1975); trifluoroacetyl peptide chloromethyl ketones, disclosed by Lestienne, et al., J. Biol. Chem. 254:5219 (1979); certain heterocyclic species disclosed by Teshima, et al., J. Biol. Chem. 257:5085 (1982); arylsulfonyl fluorides, described by Yoshimura, et al., J. Biol. Chem. 257:5077 (1982); trifluoromethylated dipeptides of formula (IV), disclosed in U.K. Patent Application 2,040,291A; and certain 2-pyridyl-1,2-benzisothiazolinone-1,1-dioxide compounds, disclosed in Jones et al., U.S. Pat. No. 4,369,183.

IV

Accordingly, new classes of potent inhibitors of serine and other proteases, characterized by longlasting inhibitory capacity and low mammalian toxicity, are potentially valuable therapeutic agents for treatment of mammalian proteolytic disease states. notably emphysema.

SUMMARY OF THE INVENTION

The present invention provides compounds of the formula or a physiologically acceptable salt thereof, wherein
$A^1$ is an amino acid of L-configuration selected from the group consisting of Ala, Pro, Gly, Glu, Leu, Lys, Phe, Ser, Val, Ile, Arg, Tyr, Thr, Asp, Asn or Gln;
$A^2$ and $A^3$ are, independently, amino acids of D or L-configuration selected from the group consisting of Ala, Arg, Asn, Asp, Cys, Gln, Glu, Gly, His, Ile, Leu, Lys, Met, Phe, Pro, Ser, Thr, Trp, Tyr or Val;
n and o are independently 0 or 1;
$R^1$ is —H or an N-terminal protecting group;
$R^2$ is an alkyl group of one to six carbons, optionally comprising an aromatic substituent, or one or more in-chain bivalent groups selected from the group consisting of —O—, —CO—, —S—, —NH—, —CONH—, —CH=CH— or —SO₂—; and
$Y^1$ and $Y^2$ are each —H, or taken together form a moiety derived from a dihydroxy compound having at least two hydroxy groups separated by at least two connecting atoms in a chain or ring, said chain or ring comprising carbon atoms, and optionally, a heteroatom or heteroatoms which can be N, S, or O;
with the proviso that where n or o is O, $R^1$ cannot be —H.

The invention also provides compositions comprising one or more of the foregoing compounds, and methods of using such compositions in treatment of aberrant proteolysis and emphysema in mammals.

DETAILED DESCRIPTION OF THE INVENTION

The compounds of the present invention are peptide derivatives of α-aminoboronic acids, and are characterized by unusual potency as inhibitors of certain proteolytic enzymes, notably neutrophil elastase. Each of the compounds of the invention comprise one or more amino acids coupled to an acid-terminal α-aminoboronic acid, which can optionally be linked to a boron-terminal protecting group —Y¹—Y²—, as illustrated by the foregoing formula.

The nature of the B-terminal protecting group —Y¹—Y²— can vary widely within the scope of the present invention. Suitable values for —Y¹—Y²— include moieties derived from compounds, principally diols, having at least two hydroxy groups separated by at least two connecting atoms in a chain or ring. Contemplated compounds within the foregoing description include, for example, pinacol, perfluoropinacol, pinanediol, ethylene glycol, diethylene glycol, catechol, 1,2-cyclohexanediol, 1,3-propanediol, 2,3-butanediol, glycerol, diethanolamine and other amino alcohols, and other equivalents apparent to those skilled in the art.

As used throughout the specification, the following abbreviations for amino acid residues or amino acids apply:
Ala=L-alanine
Arg=L-arginine
Asn=L-asparagine
Asp=L-aspartic acid
Cys=L-cysteine
Gln=L-glutamine
Glu=L-glutamic acid
Gly=Glycine
His=L-histidine
Ile=L-isoleucine
Leu=L-leucine
Lys=L-lysine
Met=L-methionine

Phe=L-phenylalanine
Pro=L-proline
Ser=L-serine
Thr=L-threonine
Trp=L-tryptophan
Tyr=L-tyrosine
Val=L-valine

Where prefixed by "D-," the foregoing abbreviations indicate an amino acid of D-configuration. "N-terminal protecting group," as used herein, refers to various amino-terminal protecting groups conveniently employed in peptide synthesis. Examples of suitable groups include acyl protecting groups, for example, formyl, acetyl (Ac), benzoyl (Bz), trifluoroacetyl, succinyl (Suc) and methoxysuccinyl (MeOSuc); aromatic urethane protecting groups, for example, benzyloxycarbonyl (Z); and aliphatic urethane protecting groups, for example, tert-butoxycarbonyl (Boc) or adamantyloxycarbonyl. Gross and Mienhofer, eds., The Peptides, Vol. 3, (Academic Press, New York 1981) pp. 3–88, disclose numerous suitable amine protecting groups.

The following represent preferred N-terminal protecting groups $R^1$;

Compounds of the invention having side-chain amino groups, for example, where $A^1$, $A^2$ or $A^3$ are Lys or Arg, can optionally comprise suitable N-terminal protecting groups attached to the side chains; similarly, amino acid residues having acidic or hydroxy side chains can be protected in the form of benzyl or other suitable esters or ethers.

As noted previously, $R^2$ refers to an alkyl group of one to six carbons, which can be straight or branched-chain. Further, $R^2$ can comprise a phenyl substituent, or optionally, one or more in-chain bivalent moieties selected from the group consisting of —O—, —CO—, —S—, —NH—, —CONH—, —CH=CH—, or —SO$_2$—. Examples of preferred values of $R^2$ include methyl, isopropyl, isobutyl, and benzyl.

Physiologically acceptable salts of the compounds of the present invention include acid addition salts, for example, hydrochloric, acetic, trifluoroacetic, succinic, citric, or other suitable acid addition salts.

Abbreviations and terms prefixed by "boro-" indicate amino acids wherein the terminal carboxyl group —CO$_2$H has been replaced by a boronic functionality Thus, "borovaline" refers to the boronic acid analogue of valine, "borophenylalanine" or "borophe" refers to the boronic acid analogue of phenylalanine, etc. In naming compounds of the invention, the protective group $-Y^1-Y^2-$ is simply identified by the name of the compound from which the group is derived, for example, pinacol or diethanolamine.

Contemplated classes of compounds within the scope of the present invention include the following. A first class includes compounds wherein $A^1$ is Ala, Pro, Gly, Val, Leu or Ile. A second class includes compounds wherein $A^1$ is Phe or Tyr. A third class includes compounds wherein $A^1$ is Lys or Arg, and a fourth class includes compounds wherein $A^1$ is Ser or Thr. Finally, a fifth class includes compounds wherein $A^1$ is Asp, Glu, Asn or Gln.

The foregoing principal classes include subclasses corresponding to preferred values of $R^2$, and these subclasses are further subtended into groups defined by preferred values for N-terminal protecting group $R^1$.

Obvious equivalents of the foregoing compounds include compounds comprising less common or modified amino acids, for example, norleucine, hydroxyproline, or other derivatives capable of incorporation into the α-aminoboronic acid peptides of the present invention.

Specific compounds within the scope of the invention, named in accordance with the conventions described above, include the following examples:
MeOSuc-AlaAlaPro-Boroval-OH,
MeOSuc-AlaAlaPro-Borophe-OH,
MeOSuc-AlaAlaPro-Boroala-OH,
MeOSuc-AlaAlaPro-Boroval-pinacol,
MeOSuc-AlaAlaPro-Borophe-pinacol,
MeOSuc-AlaAlaPro-Boroala-pinacol,
MeOSuc-AlaAlaPro-Boroala-diethanolamine,
MeOSuc-AlaAlaPro-Borophe-diethanolamine,
Z-PheGlyAla-Boroleu-OH,
Z-PheGlyAla-Boroleu-pinacol,
Z-PheGlyAla-Borophe-OH,
Boc-PheGly-Boroleu-pinacol,
Boc-PheGly-Boroleu-diethanolamine,
Boc-Ala-Boroala-pinacol,
Boc-Gly-Boroleu-pinacol,
Boc-Gly-Boroleu-diethanolamine,
Boc-PhePro-Borophe-pinacol,
MeOSuc-PheGlyLeu-Boroleu-pinacol,
Boc-D-PhePro-Boroval-pinacol,
MeOSuc-AlaAlaPro-Boroile-pinacol,
Z-PheglyPhe-Boroval-pinacol,
Z-PheGlyGlu(OBzl)-Boroval-pinacol,
Z-PheGlyLeu-Boroval-pinacol,
Z-PheGlyLeu-Boroval-diethanolamine,
Z-PheGlyLys(Boc)-Boroval-pinacol,
MeOSuc-Lys(Z)-AlaPro-Boroval-OH,
Z-PheProAla-Boroval-pinacol,
H-PheGlyGlu-Boroval-pinacol,
MeOSuc-PheGlyGlu-Boroval-pinacol,
H-PheGlySer-Boroval-pinacol,
MeOSuc-PheGlySer-Boroval-pinacol, and
Z-PheGlySer(OBzl)-Boroval-pinacol.

On the basis of superior capacity to inhibit neutrophil elastase, the compounds of the invention wherein A[1] is Pro and A[2] and A[3] are each Ala are preferred. Of these compounds, those in which the aminoboronic acid residue is borovaline, borophenylalanine, boroisoleucine, or boroalanine are most preferred.

PREPARATION: STARTING MATERIALS

Starting materials employed in synthesis of the compounds of the invention include N-protected peptides, which can be purchased from chemical suppliers, or prepared by methods well-known to those skilled in the art. In addition, esters of α-aminoboronic acids (in amine salt or free amine form) are required, which can be prepared according to the following procedure, which is a modification of the procedures disclosed by Matteson, et al., J. Am. Chem. Soc. 103:5241 (1981).

A. The first step in the synthesis of α-aminoboronic acid esters is a Grignard reaction. An alkyllithium, aryllithium, alkaryllithium, or aralkyllithium Grignard reagent is reacted with one equivalent of a trialkylborate, preferably triethylborate, forming a boronic acid 1.

The organometal Grignard reagent is prepared either by treating an alkyl, aryl, alkaryl, or aralkyl halide with lithium in a suitable solvent, e.g., ether or tetrahydrofuran, or purchased from commercial sources. The reaction of triethylborate and Grignard reagent is conducted at about −72° C. by simultaneous addition of these two reagents to a flask containing ether at about −72° C. Other solvents, e.g., tetrahydrofuran, can be used instead of ether. This procedure is substantially similar to that disclosed by Rabjohn, ed., Organic Synthesis (Wiley, New York, 1963) Coll. Vol. IV, pp. 68–72.

B. The second step in this sequence of reactions is an esterification reaction. Boronic acid 1, prepared in Step A, can be isolated for esterification, or, in the alternative, employed without isolation. Esterification is conducted by treating boronic acid 1, dissolved in ether or other suitable inert solvent, with one or more equivalents of pinacol or other suitable dihydroxy compound selected from the group previously described. This reaction can be conducted at ambient temperatures for 1 to 16 hours, yielding boronic acid ester 2.

C. This step, a homologation reaction, is conducted by treating boronic ester 2 with about one equivalent of (dichloromethyl)lithium, at about −72° C. in dimethoxyethane, tetrahydrofuran, an alkyl ether, or other suitable solvent, providing α-chloroboronic ester 3. (Dichloromethyl)lithium can be generated by reacting dichloromethane with lithium diisopropylamide, or other suitable amide, e.g., sodium dialkylamide. Lithium diisopropylamide is prepared by treating diisopropylamine with n-butyllithium in hexane in the presence of small amounts (ca 1% by weight) of tetrahydrofuran. Other amides are prepared by treating corresponding secondary amines with an alkyl metal or metal hydride in a suitable solvent. This step cannot be conducted using compounds 2 containing active hydrogen, e.g., where —Y[1]—Y[2]— is —(CH$_2$)$_2$NH(CH$_2$)$_2$—, without first blocking or protecting active hydrogens.

D. In this step, the α-chlorine atom of compound 3 is displaced with lithiohexamethyldisilizane, yielding a silylated intermediate 4. The displacement is conducted by reacting compound 3 with one equivalent of lithiohexamethyldisilazane in tetrahydrofuran at −72° C., followed by stirring the mixture for about 16 hours at 7 days at ambient temperatures. Other metals can be used in place of lithium, and other solvents, such as alkyl, ethers, are suitable. Lithiohexamethyldisilazane is prepared by treating a corresponding amine, hexamethyldisilizane, with n-butyllithium in tetrahydrofuran at about 0° C. Other disilazanes can be generated by treating corresponding amines with an alkyl metal or a metal hydride in an inert solvent at about 0° C. to about 23° C. This procedure has been previously described by Matteson, et al., J. Am. Chem. Soc. 103:5241 (1981).

E. In this step, silylated compound 4 is treated with three or more equivalents of trifluoroacetic acid in ether at 0° C., yielding a trifluoroacetic acid salt, which is a suitable starting material for synthesis of the α-aminoboronic acid peptides of the instant invention. The trifluoroacetic acid salt can be converted to a free amine by treatment with a base, e.g., alkali metal or alkaline earth metal carbonates or hydroxides, in aqueous solutions or organic/aqueous mixtures, e.g., ethanol/water or methanol/water mixtures.

PEPTIDE SYNTHESIS

Preparation of the α-amioboronic acid peptides of the present invention is illustrated by the following synthetic scheme, in which a pinacol ester of an α-aminoboronic acid is employed as a starting reagent.

Synthetic Scheme

To prepare the peptides of the present invention, an N-protected peptide is first treated with isobutyl chloroformate, to generate a mixed peptideisobutyric acid anhydride (6). An analogous procedure is disclosed by Anderson, et al., J. Am. Chem. Soc. 89:5012 (1967). Mixed anhydride 6 is subsequently coupled to a pinacol ester of an α-aminoboronic acid (in either amine salt or free amine form) in the presence of a base, e.g., triethylamine, generating an α-aminoboronic acid peptide ester 7. Pinacol esters of α-aminoboronic acid trifluoroacetic acid salts are conveniently employed due to ease of synthesis and handling. However, other ester/salt combinations can also be employed in the coupling reaction.

By-product salts of the coupling reaction are removed by filtration, and the pinacol (or other ester) peptide can be further purified by chromatography on silica gel using a suitable solvent, for example, chloroform, 1–3% methanol in chloroform, or a mixture of methanol and methylene chloride. Product peptide esters 7 can be isolated by trituration with hexane or crystallization from chloroform/hexane or ethyl acetate/hexane.

Pinacol (or other ester) peptides 7 can be converted to corresponding diethanolamine derivatives by treatment with 2–4 equivalents of diethanolamine in anhydrous tetrahydrofuran. Other esters can be generated by substitution of appropriate materials. The diethanolamine derivatives are usually crystalline. However, trituration of non-crystalline products with ether will generally yield a solid. Fractional crystallization of the diethanolamine derivatives can be employed to separate diastereomers, e.g. MeOSuc-AlaAlaPro-D-boroPhe-OH and MeOSuc-AlaAlaPro-L-boroPhe-OH.

Pentides 8 containing a free boronic acid functionality can be generated by two routes from the previously described diethanolamine or other ester derivatives. First, readily water-soluble species are treated with an excess of a cation exchange resin in protonated form in water, followed by lyophilization. Suitable resins are available from commercial sources. Second, lipophilic species can be treated with a mixture of methanol:aqueous HCl (3:2, V/V), followed by ethyl acetate extraction and removal of solvent.

UTILITY

The α-aminoboronic acid peptides of the present invention represent a novel class of potent, reversible inhibitors of metallo, acid, and serine proteases. Examples of the serine proteases inhibited by compounds within the scope of the invention include leukocyte neutrophil elastase, a proteolytic enzyme implicated in the pathogenesis of emphysema; chymotrypsin, a digestive enzyme; pancreatic elastase; and cathepsin G, a chymotryspin-like protease also associated with leukocytes. Inhibition of thermolysin, a metalloprotease, and pepsin, an acid protease, has also been demonstrated for compounds within the scope of the present invention.

As noted previously, a number of compounds have been prepared and tested for the ability to inhibit neutrophil elastase, in a continuing effort to develop therapeutic agents useful in treatment of emphysema in mammals. The most potent peptide inhibitors reported in the literature are certain chloromethyl ketone peptide analogues, disclosed by Powers, et al., Biochim. Biophys. Acta 485:156 (1977). These compounds have been reported to inhibit neutrophil elastase at a concentration of 25 μM. Several of the compounds of the present invention are analogues of chloromethyl ketone peptides previously reported; however, certain compounds of the invention have been demonstrated to inhibit neutrophil elastase at concentrations of 5–10 nM. Thus, the compounds disclosed herein are at least two to three orders of magnitude more reactive than the peptide inhibitors of corresponding amino acid sequence previously reported. This increased inhibitory capacity suggests that the compounds of the invention represent more efficient therapeutic agents for in vivo administration to mammals.

The compounds of the invention can be administered intravenously, intramuscularly, intraperitoneally, or subcutaneously to a mammal, following dispersal or solution in a pharmaceutically suitable diluent or vehicle. The compounds of the invention have been shown to possess longer-lasting inhibitory activity after administration, which is a desirable property in view of the short time-spans of inhibitory activity of compounds reported in the literature.

Additional uses for compounds of the invention include analysis of commercial reagent enzymes for active site concentration. For example, chymotrysin is supplied as a standard reagent for use in clinical quantitation of chymotrypsin activity in pancreatic juices and feces. Such assays are diagnostic for gastrointestinal and pancreatic disorders. Pancreatic elastase is also supplied commercially as a reagent for quantitation of $\alpha_1$-antitrypsin in plasma. Plasma $\alpha_1$-antitrypsin increases in concentration during the course of several inflammatory diseases, and $\alpha_1$-antitrypsin deficiencies are associated with increased incidence of lung disease. Compounds of the present invention can be used to enhance the accuracy and reproducibility of this assay by titrametric standardization of the commercial elastase supplied as a reagent.

Finally, protease activity in certain protein extracts during purification of particular proteins is a recurring problem which can complicate and compromise the results of protein isolation procedures. Certain proteases present in such extracts can be inhibited during purification steps by compounds of the invention, which bind tightly to various proteolytic enzymes.

The examples which follow illustrate particular embodiments of the invention. In the examples, "cold tetrahydrofuran" refers to tetrahydrofuran chilled in a dry-ice bath for 5–15 minutes. All percentages reported are by weight unless otherwise indicated, and all melting points are uncorrected. All temperatures are reported in degrees Celsius. Proton nuclear magnetic resonance ($^1$H NMR) chemical shifts are reported in $\delta$ units, parts per million downfield from internal tetramethylsilane standard. Various abbreviations employed in the examples include TLC, for thin-layer chromatography; MS, for mass spectrometry; FAB, for fast-atom bombardment; and CI, for chemical ionization.

Example 1: Z-PheGlyAla-Boroleu-pinacol

N-hydroxysuccinamide ester of Z-Phe-OH (4.5 g, 11.4 mmoles) was dissolved in 5 mL of dioxane and was added to a solution consisting of H-GlyAla-OH (1.85 g, 12.6 mmoles) and triethylamine (2.64 mL, 18.9 mmoles) in 5 mL of H$_2$O. The ensuing reaction was complete after 3 hours. After standing at 4° for 3 days, the resulting solution was diluted with 100 mL of 0.2N HCl, and the resulting solid was extracted into ethyl acetate. The organic phase was washed with 0.2N HCl and then with saturated aqueous NaCl containing 0.2N HCl. A solid was obtained after evaporating the organic phase. This was recrystallized from methanol:ethyl acetate (1:1, V/V) to yield a first crop (0.93 g, 2.2 mmoles, mp 171.5°–173°) and a second crop (2.75 g, 6.4 mmoles, mp 171.5°–172.5°). First and second crops: $^1$H NMR (90 MHz, C$_2$D$_6$SO): $\delta$ 1.3 (d, 3H), 2.9 (m, 2H), 3.8 (m, 2H), 4.0–4.6 (m, 2H), 4.9 (s, 2H), 7.3 (s, 10H).

Z-PheGlyAla-OH (0.653 g, 1.53 mmoles) and N-methylmorpholine (0.168 mL, 1.53 mmoles) were dissolved in tetrahydrofuran (10 mL) and were allowed to react with isobutyl chloroformate (0.199 mL, 1.53 mmoles) for 5 minutes at −20°. Cold tetrahydrofuran (10 mL) and triethylamine (0.213 mL, 1.53 mmoles) were added and the resulting mixture was added to H-Boroleupinacol•trifluoroacetate (0.50 g, 1.53 mmoles), dissolved in cold tetrahydrofuran (10 mL). This reaction mixture was stirred for approximately 1 hour at −20° and then for about 1–2 hours at 23°. At this point, the reaction mixture was filtered and the filtrate was evaporated. The remaining residue was dissolved in CHCl$_3$ and then applied to a 2 cm column containing 5 g of silica gel, previously equilibrated with CHCl$_3$. The column was sequentially eluted with CHCl$_3$, 1% methanol:CHCl$_3$ and 2% methanol:CHCl$_3$ (V:V). Fractions containing desired product, as determined by $^1$H NMR spectroscopy, were pooled and evaporated. Product was crystallized from CHCl$_3$:hexane (dissolved in CHCl$_3$ and hexane added to the cloud point), isolated, and washed with hexane to yield a solid (0.28 g; 0.45 mmole, mp 97°–98.5°). Thin-layer chromatography (TLC) in methanol:CHCl$_3$ (V:V, 1:9) on silica gel indicated a single spot, Rf. 0.48. $^1$H NMR (360 MHz, CDCl$_3$): $\delta$ 0.875 (m, 6H), 1.21 (s, 12H), 1.38 (m, 5H), 1.675 (hept, J=7 Hz, 1H), 2.85–3.03 (m, 2H), 3.1–3.25 (m, 1H), 3.7–3.95 (m, 2H), 4.4 (m, 1H), 4.63 (br., 1H), 5.02 (q, J=12 Hz, 2H), 7.1–7.35 (br., 13H). Anal. Calcd. for C$_{33}$H$_{47}$N$_4$O$_7$B: C=63.65%, H=7.62%, N=9.00%, and B=1.74%. Found: C=63.96%, H=7.70%, N=9.12%, and B=1.58%.

Example 2: Z-PheGlyAla-Boroleu-OH

Z-PheGlyAla-Boroleu-pinacol (0.210 g, 0.337 mmoles) was dissolved in tetrahydrofuran (2 mL) and diethanolamine (0.053 g, 0.506 mmoles) dissolved in tetrahydrofuran (0.88 mL) was added. After the resulting mixture was stirred overnight at room temperature, a white precipitate formed which was isolated by filtration and washed with tetrahydrofuran to yield a diethanolamine derivative (0.128 g) as an amorphous product. The filtrate was concentrated to yield additional product (0.053 g).

After removal of a 20 mg sample, the remaining diethanolamine derivative was dissolved in a mixture of methanol (3 mL) and 1.0N HCl (2 mL). The solution was stirred for 30 minutes at room temperature. Ethyl acetate (50 mL) was added and the resulting organic phase was washed with 0.2N HCl and saturated aqueous NaCl. The organic phase was dried over anhydrous Na$_2$SO$_4$, filtered, and evaporated to yield a residue (0.082 g). It was triturated with hexane to yield a white powder (0.072 g, 0.13 mmole). TLC in butanol:acetic acid:water (V:V, 4:1:1) on silica gel indicated a single spot, Rf. 0.38. $^1$H NMR (360 MHz, CDCl$_3$): $\delta$ 0.75–0.95 (br., 6H), 1.2–1.45 (br., 5H), 1.5–1.65 (br., 1H), 1.85–2.1 (br., 1H), 2.7–3.05 (br., 2H), 3.1–3.2 (br., 1H), 3.6–4.1 (br., 2H), 4.4–4.7 (br., 2H), 4.9–5.1 (br., 2H), 7.1–7.35 (br., 13H); MS (FAB): (m/z + thioglycerol) 613. Anal. Calcd. for C$_{27}$H$_{37}$N$_4$O$_7$B: C=60.00%, H=6.91%, N=10.37%, and B=2.00%. Found: C=60.17%, H=6.90%, N=10.45%, and B=2.01%.

Example 3: MeOSuc-AlaAlaPro-Boroval-pinacol

A mixed anhydride of Boc-Ala-OH was prepared by reacting Boc-Ala-OH (10 g, 52.8 mmoles) with N-methylmorpholine (5.80 mL, 52.8 mmoles) and isobutyl chloroformate (6.8 mL, 52.85 mmoles) for 5 minutes in 50 mL of tetrahydrofuran at −20°. The reaction mixture and additional N-methylmorpholine (5.8 mL) were added to H-Pro-Obzl•HCl dissolved in 50 mL of cold CHCl$_3$. After this mixture was stirred for 1 hour at −20° and 2 hours at 23°, it was filtered and the filtrate evaporated. The residue was dissolved in ethyl acetate and was washed sequentially with 0.2N HCl, 5% NaHCO$_3$, and saturated aqueous NaCl. The solvent was evaporated to yield Boc-AlaPro-OBzl as an oil (14.1 g).

H-AlaPro-OBzl•HCl was prepared by dissolving Boc-AlaPro-OBzl (14 g, 37.5 mmoles) in 100 mL of ethyl acetate and bubbling anhydrous HCl through the resulting solution for 30 minutes at 0°. This mixture was stirred for 1 hour at 23° and solvent was evaporated to yield solid (14.9 g) H-AlaPro-OBzl•HCl.

Boc-Ala-OH (11.5 g, 48.4 mmoles) was coupled to H-AlaPro-OBzl•HCl (14.9, 47.8 mmoles) by procedures substantially similar to those described above for the preparation of Boc-AlaPro-OBzl, yielding a foam, 22 g. This product crystallized from ethyl acetate to yield Boc-AlaAlaPro-OBzl (7.8 g, mp 120°–121°) in the first crop and 11.1 g (mp 111°–117°) in a second crop. First crop-Anal. Calcd. for C$_{23}$H$_{33}$N$_3$O$_6$ (mp 120°–121°): C=61.71%, H=7.45%, N=9.39%. Found: C=61.74%, H=7.56%, and N=9.46%.

MeOSuc-AlaAlaPro-OBzl was prepared by reacting Boc-AlaAlaPro-OBzl (11.5 g) with trifluoroacetic acid for 15 minutes at 23°. Trifluoroacetic acid was evaporated, and the resulting residue was treated with anhydrous HCl as described for the preparation of H-Ala-Pro-OBzl•HCl. Solvent was evaporated, and the residue was triturated with ether to yield H-AlaAla-Pro-OBzl•HCl as a white solid (9.9 g). H-AlaAlaPro-OBzl•HCl (3.78 g, 9.86 mmoles) and the N-hydroxy succinamide ester of methyl succinate, MeOSuc-OSu (2.26 g, 9.86 mmoles) were dissolved in tetrahydrofuran (15 mL). A suspension of $NaHCO_2$ (1.66 g, 19.7 mmoles) in 2.5 mL of $H_2O$ was added and the resulting solution was stirred at room temperature for 2 hours. Solvent was evaporated and the remaining residue was dissolved in ethyl acetate and was washed with 0.2N HCl and 5% $NaHCO_3$ (both solutions were prepared in saturated NaCl) and with saturated aqueous NaCl. After drying the organic phase over anhydrous $Na_2SO_4$, filtering, and concentrating by evaporation, 3.4 g of crystals (mp 122°–123°) were obtained. Anal. Calcd. for $C_{23}H_{31}N_3O_7$: C=59.84%, H=6.78%, N=9.11%. Found: C=59.80%, H=6.68%, and N=9.12%.

MeOSuc-AlaAlaPro-OH was prepared by hydrogenation of MeOSuc-AlaAlaPro-OBzl in the presence of a palladium catalyst. The benzyl ester (4.5 g, 9.7 mmoles) was dissolved in 100 mL of methanol and was hydrogenated for 1 hour in the presence of 0.5 g of 10% Pd/C in a Parr apparatus. Catalyst was removed and solvent evaporated to yield a foam (3.4 g), which was crystallized from ethyl acetate to yield 2.8 g (7.3 mmoles, mp 144°–146°) of MeOSuc-AlaAlaPro-OH, $^1$H NMR (90 MHz, $C_2D_6SO$): δ 1.17 (d, 6H), 1.6–2.3 (m, 4H), 2.5 (m+DMSO, 4H), 3.3–3.8 (s, m, 5H), 4.0–4.6 (m, 3H), 7.83–8.17 (m, 2H). Anal. Calcd. for $C_{17}H_{25}N_3O_7$: C=51.73%, H=6.80%, N=11.63%. Found: C=51.72%, H=6.92%, and N=11.13%.

MeOSuc-AlaAlaPro-OH (4.10 g, 11.05 mmoles) was dissolved in tetrahydrofuran (35 mL), activated, and coupled to H-Boroval-pinacol•trifluoroacetate (3.46 g, 11.05 mmoles) dissolved in tetrahydrofuran (15 mL) by a procedure substantially similar to that described for Z-PheGlyAla-Boroleu-pinacol (Example 2.) After filtration and evaporation of the reaction mixture, the resulting residue was dissolved in $CHCl_3$ and applied to a 3 cm column containing 30 g of silica gel previously equilibrated with $CHCl_3$. Product was eluted with $CHCl_3$ and triturated with hexane to yield a white powder (3.56 g, 6.44 mmoles). Anal. Calcd. for $C_{26}H_{45}N_4O_8B$: C=56.51%, H=8.23%, N=10.14%, and B=1.96%. Found: C=56.27%, H=8.21%, N=9.97%, and B=2.15%. Material prepared in a substantially similar experiment (E30833-8) gave $^1$H NMR (360 MHz, $CDCl_3$): δ0.85–0.95 (br., 6H), 1.20–1.24 (br., 12H), 1.25–1.28 (br., 3H), 1.33–1.38 (br., 3H), 1.8 (m, 1H), 1.95–2.075 (br., 2H), 2.2–2.3 (br., 2H), 2.5–2.55 (br., 2H), 2.65–2.75 (br., 2H), 2.9 (t, J=6 Hz, 1H), 3.69 (s, 3H), 4.65–4.85 (br., 2H); MS (FAB): (m/z+1) 553.

EXAMPLE 4: MeOSuc-AlaAlaPro-Boroval-OH

MeOSuc-AlaAlaPro-Boroval-pinacol (0.25 g, 0.452 mmoles) was dissolved in tetrahydrofuran (3.8 mL), containing diethanolamine (0.190 g, 1.81 mmoles), and the resulting solution was stirred overnight. A diethanolamine derivative (0.224 g) was precipitated by adding ether (ca. 50 mL), isolated by filtration and washed with ether.

The diethanolamine derivative and a polymeric cation exchange resin having pendant-$SO_3H$ groups in the protonated form (BioRad AG-50-X8) (0.4 g) were placed in a flask and cold $H_2O$ (2 mL) was added. The resulting mixture was allowed to warm to about 23° and stirred for 20 minutes. During this time, the solution pH changed from 7.5–8.0 to 4–5. Resin was removed and washed with two 5 mL portions of $H_2O$. The combined aqueous phase was lyophilized to yield a fluffy white solid (0.125 g, 0.27 mmole). $^1$H NMR (360 MHz, $CD_3OD$): δ 0.90–1.0 (br., 6H), 1.3–1.375 (br., 6H), 1.80 (m, 1H), 1.95–2.1 (br., 2H), 2.12–2.2 (br., 1H), 2.24–2.33 (br., 2H), 2.5–2.55 (br., 2H), 2.6–2.65 (br., 2H), 3.66 (s, 3H), 3.8 (m, 1H), 4.3–4.35 (br., 2H), 4.55–4.64 (br., 4H); MS (FAB): (m/z+thioglycerol+H+) 543. Anal. Calcd. for $C_{20}H_{35}N_4O_8B$: C=51.06%, H=7.51%, N=11.91%, and B=2.30%. Found: C=51.24%, H=7.36%, N=11.81%, and B=2.15%.

Example 5: MeOSuc-AlaAlaPro-Borophe-pinacol

MeOSuc-AlaAlaPro-OH (1.03, 2.78 mmoles) was coupled to H-Borophe-pinacol•trifluoroacetate (1.00 g, 2.78 mmoles) by a procedure substantially similar to that described for preparation of Z-PheGlyAla-Boroleupinacol (Example 1). Product was chromatographed on a 2 cm column containing 7.5 g of silica gel using $CHCl_3$ as a solvent. Fractions containing desired product were pooled and triturated with hexane, yielding white solid (0.65 g, 1.1 mmoles). $^1$H NMR (360 MHz, $CDCl_3$): 1.15–1.35 (br., 18H), 1.95–2.8 (br., 10H), 2.90–3.15 (br., 2H), 3.45–3.75 (br., 2H), 3.68 (s, 3H), 7.1–7.3 (br., 5H). Anal. Calcd. for $C_{30}H_{45}N_4O_8B$: C=59.99%, H=7.57%, N=9.33%, and B=1.80%. Found: C=59.92%, H=7.77%, N=9.28%, and B=1.61%; MS (FAB): (m/z+1) 601.

Example 6:
MeOSuc-AlaAlaPro-Borophe-diethanolamine

MeOSuC-AlaAlaPro-Borophe-pinacol (0.787 g, 1.31 mmoles) was dissolved in tetrahydrofuran (3 mL) and diethanolamine (0.207 g, 1.96 mmoles) in tetrahydrofuran (4.2 mL) was added. After 2 hours, the pinacol derivative could not be detected by thin-layer chromatography (TLC). Solvent was evaporated and the partially crystalline residue was extracted with hot ethyl acetate to yield a solid (0.29 g, 0.5 mmole, mp 184°–185°, E 30833-39). $[α]_D^{25} = -81.6±2.0°$, C=1% in ethanol. Anal. Calcd. for $C_{28}H_{41}N_5O_8B$ (E30833-28, prepared by a similar procedure): C=57.33%, H=7.06%, N=11.94%, and B=1.84%. Found: C=57.06%, H=7.21%, N=11.77%, and B=1.83%.

An additional crop of crystals was obtained from ethyl acetate (0.04 g, 0.07 mmole, mp 187.5°–188.5°).

The residue from the foregoing crystallization procedures was triturated with ether to yield a white amorphous solid (0.29 g, 0.5 mmole, 2-E30833-39). $[α]_{25}^D = -92.8±2.0°$. $^1$H NMR (360 MHz, $CD_3OD$): δ 1.25–1.4 (br., 6H), 2.45–2.65 (br., 4H), 2.65–2.8 (br., 4H), 2.7–2.85 (br., 3H), 2.85–3.05 (br., 2H), 3.65 (s,3H), 3.8–4.0 (br., 4H), 7.10–7.31 (br., 5H). Anal. Calcd. for $C_{28}H_{41}N_5O_8B$: C=57.33%, H=7.06%, N=11.94%, and B=1.84%. Found: C=57.32%, H=7.15%, N=11.79%, and B=1.61%. MS (FAB): (m/z+1) 587.

Example 7: MeOSuc-AlaAlaPro-Borophe-OH

MeOSuc-AlaAlaPro-Borophe-diethanolamine (0.20 g, 0.34 mmole) (Example 6) was placed in a flask with approximately a twofold excess (0.4 g) of a polystyrene substituted sulfonic acid resin in the protonated form (Bio-Rad AG-50-X8), and 2 mL of cold water were added. The resulting mixture was allowed to stir for 10 minutes while coming to room temperature. Resin was removed and washed with two 5 mL portions of $H_2O$. The combined aqueous fractions were lyophilized to yield a white powder. The foregoing procedure yielded 0.135 g (0.26 mmole) of the free boronic acid. Material prepared by a substantially similar synthesis yielded the following observations: $^1H$ NMR (360 MHz, $CDCl_3$): δ 1.25–1.38 (br., 6H), 1.9–2.3 (br., 4H), 2.48–2.55 (br., 2H), 2.55–2.7 (br., 2H), 2.82–2.91 (br., 2H), 3.65 (s, 3H), 3.80 (m, 1H), 4.35 (m, 1H), 4.58 (m, 1H), 7.15–7.3 (br., 5H). Anal. Calcd. for $C_{24}H_{38}N_4O_8B$: C=55.60%, H=6.82%, N=10.81%, B=2.09%. Found: C=55.84%, H=6.76%, N=10.72%, B=2.07%

Example 8: MeOSuc-AlaAlaPro-Boroala-pinacol

MeOSuc-AlaAlaPro-OH (3.25 g, 8.77 mmoles was coupled to H-Boroala-pinacol•trifluoroacetate (2.50 g, 8.77 mmoles) by a procedure substantially similar to that described for Z-PheGlyAla-Boroleu-pinacol (Example 1). Product was purified by chromatography on silica gel, using $CHCl_3$ as a solvent, to yield a solid (2.2 g). A principal fraction (1.3 g) was triturated with hexane to yield 1.03 g (1.96 mmoles) of a white solid; $^1H$ NMR (90 MHz, $CDCl_3$): δ 0.8–1.4 (br., 21H), 1.8–2.3 (br., 4H), 2.4–3.0 (br., 5H), 3.5–3.8 (br., 2H), 3.65 (s, 3H), 4.4–4.9 (br., 3H). Anal. Calcd. for $C_{24}H_{41}N_4O_8B$: C=54.95%, H=7.81%, N=10.68%, and B=2.06%. Found: C=55.06%, H=8.04%, N=9.64%, and B=2.00%. C=54.73%, H=8.12% and N=10.58%.

Example 9: MeOSuc-AlaAlaPro-Boroala-diethanolamine

MeOSuc-AlaAlaPro-Boroala-pinacol (0.866 g, 1.65 mmoles) was reacted with with diethanolamine (0.260 g, 2.48 mmoles) in tetrahydrofuran (5.2 mL) for 4 days at 23°. A white precipitate formed, which was isolated and washed with tetrahydrofuran, yielding a crystalline solid (0.35 g, 0.68 mmole, mp 172.5°–175°). $^1H$ NMR (80 MHz, $CDCl_3$): δ 1.0–1.56 (br., 9H), 1.7–2.4 (br., 4H), 2.4–3.5 (br., 9H), 3.7 (s, 3H), 3.5–4.1 (br., 6H), 4.25–5.0 (br., 3H); Anal. Calcd. for $C_{22}H_{38}N_5O_8B$: C=51.66%, H=7.50%, N=13.70%, and B=2.11%. Found: C=51.54%, H=7.56%, N=13.62%, and B=2.17%.

Filtrate from the foregoing isolation was evaporated and triturated with ether to yield 0.270 g (0.53 mmole) of an amorphous white solid. The $^1H$ NMR spectrum obtained corresponded to that expected for the desired product. Biological activity, measured as capacity for inhibition of pancreatic elastase, was at least 5-fold greater for the crystalline sample, suggesting that two diastereomeric forms had been separated or partially separated, and that the crystalline sample was principally the L-diastereomer.

Example 10: MeOSuc-AlaAlaPro-Boroala-OH

MeOSuc-AlaAlaPro-Boroala-diethanolamine (0.20 g, 0.381 mmole) was dissolved in cold water (2 mL) and the previously described cationic exchange resin (0.45 g) was added. After allowing this mixture to warm to about 23°, the resin was removed and washed with water (2×5 mL). The aqueous fractions were lyophilized to yield product (0.15 g, 0.34 mmole). $^1H$ NMR (80 MHz, $CDCl_3$): δ 1.03 (d, J=7 Hz, 3H), 1.2–1.5 (br., 6H), 1.8–2.3 (br., 4H), 2.4–3.01 (br., 5H), 3.7 (s, 3H), 4.3–5.0 (br., 3H). The sample was triturated with hexane to yield an analytical sample. Anal. Calcd. for $C_{18}H_{31}N_4O_8B$: C=48.87%, H=7.08%, N=12.67% and B=2.44%. Found: C=49.00%, H=6.96%, N=12.50% and B=2.41%.

Example 11: Boc-PhePro-Borophe-pinacol

N-hydroxysuccinamide ester of Boc-Phe-OH (10.0 g, 27.6 mmoles) was dissolved in 1,2-dimethoxyethane (375 mL) and a solution of H-Pro-OH (4.76 g, 41.4 mmoles) and $NaHCO_3$ (4.83 g, 82.6 mmoles) in 175 mL of $H_2O$ was added. The resulting mixture was stirred overnight at about 23°, and then evaporated to dryness. The resulting residue was dissolved in 100 mL of $H_2O$ and filtered. Filtrate was acidified with HCl and product was extracted into $CHCl_3$. The $CHCl_3$ extract was dried over $Na_2SO_4$ and solvent was evaporated, yielding an oil. The oil was triturated with hexane to provide an amorphous white solid (8.7 g, 23 mmoles). $^1H$ NMR (90 MHz, $CDCl_3$): δ 1.37 (s, 9H), 1.5–2.3 (m, 4H), 2.9–3.3 (m, 2H), 3.3–3.8 (m, 2H), 4.43–4.80 (m, 2H), 5.6 (m, 1H) and 7.27 (s, 5H).

Boc-PhePro-OH (4.02 g, 11.1 mmoles) was activated in tetrahydrofuran (25 mL) and coupled to H-Borophe-pinacol•trifluoroacetate (4.00 g, 11.1 mmoles) dissolved in tetrahydrofuran (10 mL), using a procedure substantially similar to that described for synthesis of Z-PheGlyAla-Boroleu-pinacol (Example 1). Chromatography of the resulting mixture on silica gel provided an oil (4.9 g). The oil (3.6 g) was triturated with hexane to yield the desired product (0.86 g, 1.45 mmoles, mp 81.5°–83.5° C.). $^1H$ NMR (90 MHZ) in $CDCl_3$: δ 1.2 (s, 12H), 1.35 (s, 9H), 1.5–2.5 (br, 4H), 2.5–3.7 (br., 7H), 4.3–4.8 (br., 2H), 4.9–5.3 (br., 1H), 6.7–7.5 (s, br, 11H). Anal. Calcd. for $C_{33}H_{46}N_3O_6B$: C=66.99%, H=7.85%, N=7.10%, and B=1.83%. Found: C=66.74%, H=8.16%, N=7.15%, and B=1.79%.

Example 12: MeOSuc-PheGlyLeu-Boroleu-pinacol

Boc-PheGlyLeu-OH was prepared by coupling the N-hydroxysuccinamide ester of Boc-Phe-OH (14.1 g, 39.0 mmoles) to H-Gly-Leu-OH (8.1 g, 42.9 mmoles) using a procedure substantially similar to that described for preparation of Boc-PhePro-OH (Example 11). Product was crystallized from ethyl acetate (14.4 g).

Anal. Calcd. for $C_{22}H_{33}N_3O_6$: C=60.66%, H=7.66%, N=9.65%. Found: C=60.25%, H=7.51% and N=9.63%.

H-PheGlyLeu-OH•trifluoroacetate was prepared by treating Boc-PheGlyLeu-OH with trifluoroacetic acid for 5 min at about 23°, followed by evaporation and drying in vacuo with KOH.

H-PheGlyLeu-OH.trifluoroacetate (10.3 g, 23.0 mmoles), N-hydroxysuccinamide ester of methoxysuccinate (5.27 g, 23.0 mmoles), and triethylamine (8.0 mL, 57.5 mmoles) were dissolved in N,N-dimethylformamide (15 mL) and allowed to react at 0° C. The resulting reaction mixture was diluted with N,N-dimethylformamide (10 mL) and was stirred at 23° for ~30 min. The reaction mixture was concentrated to about 5 mL by evaporation, diluted with 75 mL of 5% $NaHCO_3$, and extracted with ethyl acetate. The resulting aqueous phase was acidified with HCl. Product was extracted into ethyl acetate and washed sequentially with 0.2N HCl and saturated aqueous NaCl adjusted to 0.2N HCl. After drying over $Na_2SO_4$, filtering, and concentrating, crystals (5.73 g, 12.39 mmoles, mp 167.5°–169°) were obtained.

In a substantially similar experiment, the following analysis was obtained for MeOSuc-PheGlyLeu-OH (mp 167.5°-168.5°).

Anal. Calcd. for $C_{23}H_{32}N_3O_7$: C=58.91%, H=6.76%, and N=9.37%. Found: C=59.20%, H=6.99%, and N=9.06%.

MeOSuc-PheGlyLeu-OH (0.897 g, 2.0 mmoles) was dissolved in tetrahydrofuran (15 mL) containing N-methylmorpholine (0.22 mL, 2.0 mmoles) and was allowed to react with isobutyl chloroformate (0.26 mL, 2.0 mmoles) for 5 minutes at −20° Cold tetrahydrofuran (10 mL) and triethylamine (0.28 mL, 2.0 mmoles) were added and the resulting mixture was immediately added to a solution of H-Boroleu-pinaco.trifluoroacetate (0.65 g, 2.0 mmoles) in 10 mL of cold tetrahydrofuran. After stirring for approximately 1 hour at −20° and 2 hours at 23°, the resulting mixture was filtered, and the filtrate evaporated to dryness. The remaining residue was dissolved in ethyl acetate and then washed sequentially with 0.2N HCl, 5% NaHCO3, and saturated aqueous NaCl. The organic phase was dried over anhydrous $Na_2SO_4$, filtered and evaporated to yield 450 mg of material. TLC in methanol:chloroform (V:V, 1:9) indicated three spots, Rfs 0.62, 0.54, 0.50, on silica gel plates.

This material was dissolved in tetrahydrofuran (10 mL) and pinacol (0.13 g, 0.71 mmole) was added. The resulting solution was stirred overnight, but no significant change in TLC results was observed. Solvent was evaporated and the remaining residue was applied to a 2 cm column containing 10 g of silica gel and equilibrated with $CHCl_3$. The column was stepwise eluted, first with $CHCl_3$ and then $CHCl_3$ containing 2% methanol. Three fractions (0.21 g, 0.33 mmole) were collected which showed predominantly one spot at Rf 0.50 by TLC. $^1H$ NMR (90 MHZ) in $CDCl_3$: δ 0.90 (m, 12H), 1.17 (s, 9H), 1.27-2.1 (br., 8H), 2.1-3.5 (br., 8H), 3.60 (s, 3H), 3.9 (m, 2H), 4.6 (m, 2H), and 6.8-7.9 (br., 10H).

Example 13: Boc-Ala-Boroala-pinacol

Boc-Ala-OH (0.664 g, 3.51 mmoles) was coupled to H-Boroala-pinacol.trifluoroacetate (1.00 g, 3.51 mmoles) by a procedure substantially similar to that described for preparation of Z-PheGlyAla-Boroleupinacol (Example 1). Crude product was chromatographed on a 2 cm column containing 7.5 g of silica gel, using $CHCl_3$ as solvent. Product (0.86 g) was crystallized from $CHCl_3$:hexane, (0.70 g, 2.05 mmoles, mp 122.5-124°). TLC in methanol:$CHCl_3$ (V:V, 1:9) indicated a single spot Rf 0.49; $^1H$ NMR (360 MHz, $CDCl_3$): δ 1.15-1.18 (d, d, J=4.5, 8 Hz, 3H), 1.24 (s, 12H), 1.38 (d, d, J=6.1 Hz, 3H), 1.45 (s, 9H), 2.95 (m, 1H), 4.25 (m, 1H), 5.15 (br., 1H); Anal. Calcd. for $C_{16}H_{31}N_2O_5B$: C=56.14%, H=9.15%, N=8.19%, and B=3.16%. Found: C=55.90%, H=9.12%, N=7.97%, and B=3.21%.

Example 14: Boc-Ala-Boroala-diethanolamine

Boc-Ala-Boroala-pinacol (0.430 g, 1.26 mmoles) was dissolved in 4 mL of tetrahydrofuran, and then treated with diethanolamine (0.198 g, 1.88 mmoles) dissolved in tetrahydrofuran (4 mL). After about 3 hours, the pinacol starting material could not be detected by TLC. Solvent was evaporated and the residue was crystallized from ethyl acetate:hexane, providing 0.18 g (0.55 mmoles, mp 174°-174.5°); $^1H$ NMR (360 MHz, $CDCl_3$): δ 1.23 (d, J=9 Hz, 3H), 1.34 (d, J=8 Hz, 3H), 1.44 (s, 9H), 2.7-2.8 (br., 2H), 3.0-3.15 (br., 2H), 3.35 (m, 1H), 3.8-4.03 (br., 4H), 4.05 (m, 1H). Anal. Calcd. for $C_{14}H_{28}N_3O_5B$: C=51.07%, H=8.59%, N=12.76%, and B=3.28%. Found: C, 51.06%, H=8.32%, N=12.76% and B=3.64%.

Example 15: Boc-Gly-Boroleu-pinacol

A solution of Boc-Gly-OH (0.350 g, 2 mmoles) in methylene chloride (20 mL) was treated with N-methylmorpholine (0.202 g, 0.219 mL, 2 mmoles), and then cooled in an ice/acetone bath at −15°. Isobutyl chloroformate (0.273 g, 0.262 mL, 2 mmoles) was added and the resulting reaction mixture was stirred for 5 minutes. A solution of H-Boroleu-pinacol.trifluoroacetate (0.654 g, 2 mmoles) in 10 mL of methylene chloride containing triethylamine (0.202 g, 0.278 mL, 2 mmoles) was added and the reaction mixture was allowed to warm to about 23°. The reaction mixture was stirred for 1.5 hrs., diluted with 100 mL of methylene chloride and then washed with 20 mL of 10% HCl, followed by 20 mL of a saturated sodium bicarbonate solution. Drying the solution over $Na_2SO_4$ and concentrating gave a liquid (0.70 g) which was chromatographed on silica gel using 9:1 methylene chloride:methanol (V:V) as eluent to provide a solid product (0.474 g, 1.28 mmoles), 67°-70°, $^1H$ NMR (360 MHz, $CDCl_3$): δ 0.91 (br., 6H), 1.23 (s, 12H), 1.41 (t, J=7 Hz, 2H), 1.45 (s, 9H), 1.61 (hept, J=7 Hz, 1H), 2.98 (br., 1H), 3.84 (d, J=6 Hz, 2H), 5.8 (br., 1H), 6.86 (br., 1H). Anal. Calcd. for $C_{18}H_{35}N_2O_5B$: C=58.38%, H=9.53%, N=7.57%, B=2.92%. Found: C=58.39%, H=9.44%, N=7.03%, B=3.08%.

Example 16: Boc-Gly-Boroleu-diethanolamine

A solution of Boc-Gly-Boroleu-pinacol (0.240 g, 0.65 mmole) in isopropanol (10 mL) was treated with diethanolamine (0.071 g, 0.70 mmole). The reaction mixture was allowed to stand for 5 days, evaporated and dissolved in warm ether. A solid (0.02 gl), mp 214°-216° was obtained on cooling to about 23°. The remaining solution was treated with additional diethanolamine (71 mg, 0.7 mmole) in isopropanol (0.7 mL) and stirred for 48 hours, yielding a white solid (150 mg, 0.42 mmole), mp 215°-219°. $^1H$ NMR (360 MHz, $CDCl_3$): δ 0.85 (d, J=6 Hz, 3H), 0.90 (d, J=6 Hz, 3H), 1.45 (s, 9H), 1.4-1.6 (br., 3H), 2.7-2.8 (br., 2H), 3.03-3.15 (br., 2H), 3.38 (m, 1H), 3.65-3.80 (br., 2H), 3.83-3.9 (br., 2H), 3.93-4.02 (br., 2H), 5.2 (br., 1H), 6.23 (br., 1H), 6.85 (br., 1H). Anal. Calcd. for $C_{16}H_{32}N_3O_5B$: C=53.79%, H=9.03%, N=11.76%, B=3.03%. Found: C=53.87%, H=9.25% N=11.69%, B=3.09%.

Example 17: Boc-PheGly-Boroleu-pinacol

Boc-Phe-OH (25.0 g, 94.0 mmoles) was coupled to H-Gly-OCH3.HCl (12.0 g, 94.0 mmoles) using a mixed anhydride procedure substantially similar to that described by *J. Am. Chem. Soc.* 89:5012 (1967). 35.1 g of a colorless oil was obtained, which crystallized upon standing. This product was recrystallized from 50 mL of hot ethyl acetate, to which 100 mL of ether and 100 mL of hexane were added. Additional hexane was added as crystallization proceeded to give 20.80 g (62 mmoles, 66%), mp 94.6°-96.3° of Boc-PheGly-OMe. An additional 5.9 g (18 mmoles, 19%) mp 93.8°-96.1° was obtained by reprocessing the residue.

Anal. Calcd. for $C_{17}H_{24}N_2O_5$: C, 60.70%; H, 7.19%; N, 8.33%. Found: C, 61.42%; H, 7.13%; N, 8.66%; C, 61.43%; H, 7.24%; N, 8.55%.

A solution of 16.8 g (50 mmole) of Boc-PheGly-OMe in 250 mL of methanol was treated with 120 mL of 0.5N aqueous sodium hydroxide. The resulting solution was stirred for 2 hrs, stripped to a volume of about 100 mL, and extracted with $CH_3Cl$. $CH_3Cl$ was removed, and the resulting solution was acidified to pH 5 with 57 mL of 1N HCl. A sticky solid precipitate resulted, which solidified to provide a white powder which was filtered, water-washed, and vacuum-dried, yielding 15.01 g (46.6 mmoles) of crude product. A portion, recrystallized from ethyl acetate/hexane, melted at 164.6°–165.6°, $\alpha_D^{25} = -9.4°$, C=1.03 acetone.

Anal. Calcd. for $C_{16}H_{22}N_2O_5$: C, 59.61%; H, 6.88%, N, 8.69%. Found: C, 59.76%; H, 6.86%; N, 8.87%.

A solution of Boc-PheGly-OH (0.645 g, 2 mmoles) in tetrahydrofuran (15 mL) was treated with N-methylmorpholine (0.202 g, 0.220 mL, 2 moles), cooled to $-15°$, and then treated with isobutylchloroformate (0.273 g, 0.26 mL, 2 mmoles). The resulting reaction mixture was stirred for 5 min. at $-15°$ and treated with triethylamine (0.202 g, 0.279 mL, 2 mmoles), followed by a solution of H-Boroleu-pinacol.trifluoroacetate (0.652 g, 2 mmoles) in tetrahydrofuran (5 mL). The resulting reaction mixture was warmed to about 23° and stirred for 1 hour. The mixture was then diluted with 100 mL of methylene chloride, washed with 25 mL of 5% HCl, followed by 25 mL of saturated sodium bicarbonate solution. Drying the resulting solution over sodium sulfate, followed by concentrating under reduced pressure, provided a crude product (1.24 g), which was chromatographed on silica gel using 9:1 methylene chloride:methanol (V:V), yielding a pure product (0.911 g, 1.76 mmoles). $^1$H NMR (360 MHz, $CDCl_3$): $\delta$ 0.88–0.93 (br., 6H), 1.22 (s, 12H), 1.38 (two peaks, 9H), 1.4–1.45 (br., 2H), 1.7 (hept, J=7 Hz, 1H), 2.75–3.45 (br., 3H), 3.9–4.15 (br., 2H), 4.20 (m, 1H), 7.15–7.35 (br., 5H). Anal Calcd. for $C_{27}H_{44}N_3O_6B$: C=62.67%, H=8.57%, N=8.12%, B=2.09%. Found: C=62.51%, H=8.81%, N=7.69%, B=2.37%. MS (CI): (m/z) 517.

Example 18: Boc-PheGly-Boroleu-diethanolamine

A solution of Boc-PheGly-Boroleu-pinacol (0.178 g, 0.344 mmole) in ether (5 mL) was treated with diethanolamine (0.070 g, 0.7 mmole). The resulting solution was stirred for 48 hours; during this period, crystals formed which were filtered from solution: (0.20 g, 0.4 mmole), mp 169°–176°. $^1$H NMR (360 MHz, $CDCl_3$): $\delta$ 0.83 (d, J=6 Hz, 3H), 0.90 (d, J=6 Hz, 3H), 1.35–1.4 (br., 9H), 1.35–1.45 (br., 1H), 1.53–1.65 (br., 2H), 2.7–2.8 (br., 2H), 2.9–3.2 (br., 4H), 3.3–3.4 (br., 1H), 3.6–3.78 (br., 2H), 3.8–4.0 (br., 4H), 4.35 (m, 1H), 7.1–7.35 (br., 5H). Anal. Calcd. for $C_{25}H_{40}N_4O_6B$: C=59.60%, H=8.01%, N=11.13%, B=2.15%. Found: C=59.36%, H=8.29%, N=10.98%, B=2.05%.

Example 19: H-PheGly-Boroleu-pinacol.trifluoroacetate

A solution of Boc-PheGly-Boroleu-pinacol (0.240 g, 0.464 mmole) was dissolved in 2 mL of trifluoroacetic acid and stirred for 15 minutes. The resulting solution was concentrated under reduced pressure, providing an oil. $^1$H NMR (360 MHz, $CDCl_3$): $\delta$ 0.83–0.88 (br., 6H), 1.25–1.3 (br., 2H), 1.26 (s, 9H), 1.55 (hept., J=7 Hz, 1H), 2.75 (t, J=9 Hz, 1H), 3.1–3.2 (br., 2H), 3.88 (m, 1H), 4.26 (d, d, J=16, 8 Hz, 1H), 4.35 (m, 1H), 7.15–7.4 (br., 5H). MS (FAB): (m/z—$CF_3COO$) 418.

Example 20: H-PheGlyGlu-Boroval-pinacol.$CH_3COOH$

This compound was prepared by catalytic hydrogenation of Z-PheGlyGlu(OBzl)-Boroval-pinacol, prepared substantially according to the procedure of Example 5. Z-PheGlyGlu(OBzl)-Boraval-pinacol (0.60 g, 0.79 mmol) was dissolved in 10 ml absolute ethanol, to which 0.50 mL glacial acetic acid and 0.40 g of 10% Pd on carbon were added. Hydrogen was bubbled through the foregoing mixture for 4 hours at approximately 23°. The resulting reaction mixture was permitted to stand under a blanket of $N_2$ overnight. Catalyst was removed by filtration, and solvent was evaporated, yielding an oil which was triturated with ether to provide a solid (0.20 g.) Anal. Calcd. for $C_{28}H_{45}N_4O_9B$: C=56.75%, H=7.67%; N=9.46%, B=1.82%. Found: C=56.47%, H=7.59%, N=9.69%, B=1.95%.

Example 21: MeOSuc-PheGlyGlu-Boroval-pinacol

H-PheGlyGlu-Boroval-pinacol.$CH_3COOH$, prepared substantially by the procedure described in Example 5, (0.10 g, 0.17 mmol) was dissolved in 2.0 mL THF and 0.038 g (0.17 mmol) N-hydroxysuccinimide ester of methoxysuccinate, 0.028 g (0.337 mmol) sodium bicarbonate, and 0.5 mL water were added. After 15 minutes, 0.014 g (0.17 mmol) additional $NaHCO_3$ were added and the resulting reaction mixture stirred 1.5 hour at approximately 23°. The reaction mixture was then diluted to 50 mL with 0.2N HCl in saturated NaCl and product extracted into ethyl acetate. The resulting organic layer was dried over $Na_2SO_4$, filtered, and solvent evaporated, yielding 70 mg of crude product. This material was dissolved in chloroform and slowly evaporated to dryness to provide a crystalline product, which was isolated and washed with ether to yield 0.040 g of the desired product, m.p. 152°–153°. Anal. Calcd. for $C_{31}N_{47}N_4O_{10}B$: C=57.58%, H=7.34%, N=8.67%, B=1.67%. Found: C=57.47%, H=7.22%, N=8.51%, B=1.61%.

Examples 22–34: Additional Peptides

The following compounds were prepared by procedures substantially similar to the indicated examples.

| Example | Compound | Prepared according to Example: |
|---|---|---|
| 22 | Boc—D-PhePro—Boroval—pinacol | 5 |
| 23 | MeOSuc—AlaAlaPro—Boroile—pinacol | 5 |
| 24 | Z—PheGlyPhe—Boroval—pinacol | 5 |
| 25 | Z—PheGlyGlu(OBzl)—Boroval—pinacol | 5 |
| 26 | Z—PheGlyLeu—Boroval—pinacol | 5 |
| 27 | Z—PheGlyLeu—Boroval—diethanolamine | 6 |
| 28 | Z—PheGlyLys(Boc)—Boroval—pinacol | 5 |
| 29 | Z—PheGlyLys—Boroval—pinacol.trifluoroacetate | 5,19 |
| 30 | MeOSuc—Lys(Z)—AlaPro—Boroval—OH | 5,6 |
| 31 | Z—PheProAla—Boroval—pinacol | 5 |
| 32 | H—PheGlySer—Boroval—pinacol.$CH_3COOH$ | 20 |
| 33 | MeOSuc—PheGlySer—Boroval—pinacol | 21 |
| 34 | Z—PheGlySer(OBzl)—Boroval—pinacol | 5 |

Example 35: Inhibition of Neutrophil Elastase

Neutrophil elastase was prepared by the procedure described by Baugh. et al., Biochemistry 15:836 (1979). Enzyme assays were conducted substantially according to the procedure disclosed by Nakajima, et al., J. Biol.

Chem. 254:4027 (1979), in assay mixtures containing 0.10M Hepes (N-2-hydroxyethylpiperazine-N'-2-ethanesulfonic acid) buffer, pH 7.5; 0.5M NaCl; 10% dimethylsulfoxide; and $1.50 \times 10^{-4}$M MeOSuc-AlaAla-Pro-Val-p-nitroanilide as substrate. Inhibitors were evaluated by comparing enzymatic activity measured in the presence and absence of inhibitor. Results are set forth in Table 2, below.

A more extensive evaluation of the kinetic constants for interaction of human neutrophil elastase with MeO-Suc-AlaAlaPro-Boroval-OH were determined by methods substantially similar to those disclosed by Schloss, et al., Biochemistry 19:2358 (1980), who describe the following equation describing reversible, tight binding inhibition:

As determined herein, $K_i$ (initial)$=k_2/k_1$; $K_i$ (final)$=(k_2/k_1)k_4/(k_3+k_4)$; and $K_i$ (final)$>K_i$ (initial); E=[Enzyme]; I=[inhibitor]; EI and EI*=[enzyme-inhibitor complexes].

$K_i$(initial) was determined from initial velocity studies, according to the method of Lineweaver and Burk. Substrate concentration was varied from 0.80–0.04 mM, and concentration of inhibitor (MeOSuc-AlaAlaPro-Boroval-OH) was 200 nM. Observed inhibition appeared to be competitive, since double reciprocal plots of initial velocity vs. substrate concentration intercepted the y-axis at the same point. The results of these studies are set forth in Column A of Table 1, below.

Values of $K_i$ (initial) and $K_i$ (final) were determined from observations of progressive inhibition of elastase in the presence of $2.0 \times 10^{-4}$M substrate measured in the presence of 30–300 nM MeOSuc-AlaAlaPro-Boroval-OH. The data were fitted to the following equation: $P=P_0+(v_i-v_f)/k+v_ft+(v_f-v_i)e^{-kt}/k$. P is the concentration of product at time t, $v_i$ is the initial velocity, $v_f$ is the final steady state velocity, k is the first order rate constant and $P_0$ is the concentration of product at t=0. Values of $K_i$(initial) and $K_i$(final) were then determined from plots of velocity$^{-1}$ vs. concentration of inhibitor using the method described by Dixon, Biochem. J. 55:170 (1953). Results are set forth in Column B of Table 1, below.

TABLE 1

Kinetic Properties of the Interaction of Human Neutrophil Elastase with MeOSuc—AlaAlaPro—Boroval—OH

|  | A | B |
|---|---|---|
|  | Ki (nM) | Ki (nM) |
| Initial | 150 | 91 (t = 0) |
| Final | — | 6.2 (t = ∞, equilibrium) |

TABLE 2

Inhibition of Human Neutrophil Elastase

| Inhibitor | Conc. (nM) | Times (min) | % Activity[a,c] |
|---|---|---|---|
| MeOSuc—Ala—Ala—Pro—Boroval—OH | 100 | 0.5 | 61 |
|  |  | 2 | 36 |
|  |  | 4 | 27 |
| MeOSuc—Ala—Ala—Pro—Borophe—OH | 500 | N.T[b] | 55 |
| MeOSuc—Ala—Ala—Pro—Boroala—OH | 100 | N.T | 64 |
| Z—Phe—Gly—Ala—Boroleu—OH | 200 | N.T | 73 |
| MeOSuc—Ala—Ala—Pro—Boroval—pinacol | 10,000 | 0.5 | 61 |
|  |  | 2 | 30 |
|  |  | 4 | 11 |
| MeOSuc—Ala—Ala—Pro—Borophe—pinacol | 10,000 | 1 | 41 |
|  |  | 7 | 24 |
| MeOSuc—Ala—Ala—Pro—Boroala—pinacol | 1,000 | 0.5 | 71 |
|  |  | 4 | 38 |
| Z—Phe—Gly—Ala—Boroleu—pinacol | 3,000 | 0.5 | 46 |
|  |  | 4 | 30 |
| Boc—Phe—Pro—Borophe—pinacol | 5,000 | 0.5 | 42 |
|  |  | 2 | 23 |
|  |  | 4 | 17 |

[a]Activity (rate) of the control (0% inhibitor) was 0.0147 min$^{-1}$, measured by change in optical density of sample at 405 nm.
[b]N.T. No detectable time dependence in inhibition could be detected during the 3–4 min assay period.
[c]Activity = activity (rate) as a percentage of control value.

Additional peptide inhibitors were evaluated by a procedure similar to that described above. Stock solutions of inhibitors (1.00 mM) were prepared in dimethylsulfoxide and compounds were diluted to 0.10 mM with 0.10 mM sodium phosphate buffer, pH 7.5, yielding the free boronic acid. After incubation for one hour at about 23°, inhibitors were added to assay solutions (2.00 mL) consisting of 0.020M MeOSuc-Ala-AlaProVal-p-nitroanilide in 0.10M Hepes buffer, pH 7.5, containing 0.50M NaCl. Assays were initiated by addition of 0.50 µg neutrophil elastase. Control assays without inhibitor indicated an initial velocity of 0.0195 min$^{-1}$. The value "k" in Table 3, below, is an estimate of the first order rate constant for time-dependent inhibition, as described above for MeOSuc-AlaAlaPro-Boroval-OH (Table 1). Results are set forth in Table 3, below:

TABLE 3

Inhibition of Human Neutrophil Elastase

| Compound | Conc. (M) | % Initial Activity | k (min$^{-1}$) |
|---|---|---|---|
| MeOSuc—Ala—Ala—Pro—Boroval—OH | $1.0 \times 10^{-7}$ | 61 | 0.27 |
| MeOSuc—Ala—Ala—Pro—Boroile—OH | $1.0 \times 10^{-7}$ | 60 | 0.28 |
| MeOSuc—Lys(Z)—Ala—Pro—Boroval—OH | $5.0 \times 10^{-8}$ | 59 | 0.54 |
| Z—Phe—Gly—Ser(OBzl)—Boroval—OH | $1.25 \times 10^{-7}$ | 66 | 0.17 |
| MeOSuc—Phe—Gly—Ser—Boroval—OH | $5.0 \times 10^{-7}$ | 78 | 0.26 |
| H—Phe—Gly—Ser—Boroval—OH | $1.0 \times 10^{-6}$ | 75 | a |
| Z—Phe—Gly—Glu(OBzl)—Boroval—OH | $1.0 \times 10^{-7}$ | 61 | 0.20 |
| MeOSuc—Phe—Gly—Glu—Boroval—OH | $1.0 \times 10^{-6}$ | 52 | 0.18 |
| H—Phe—Gly—Glu—Boroval—OH | $2.0 \times 10^{-6}$ | 54 | a |
| Z—Phe—Gly—Lys(Boc)—Boroval—OH | $2.0 \times 10^{-7}$ | 55 | 0.37 |
| Z—Phe—Gly—Lys—Boroval—OH | $2.5 \times 10^{-7}$ | 67 | 0.28 |
| Z—Phe—Gly—Phe—Boroval—OH | $2.0 \times 10^{-7}$ | 47 | 0.18 |
| Z—Phe—Gly—Leu—Boroval—OH | $2.0 \times 10^{-7}$ | 62 | 0.26 |

TABLE 3-continued

| | Inhibition of Human Neutrophil Elastase | | |
|---|---|---|---|
| Compound | Conc. (M) | % Initial Activity | k (min$^{-1}$) |
| Z—Phe—Pro—Ala—Boroval—OH | $4.0 \times 10^{-6}$ | 51 | a |
| Boc—D-Phe—Pro—Boroval—OH | $2.0 \times 10^{-7}$ | 54 | 0.35 | a No significant time dependence was observed at the level of inhibitor tested.

Example 36: Inhibition of Pancreatic Elastase

Porcine pancreatic elastase (9.8 U/mg.) was obtained from commercial sources. The enzyme was assayed in 2.00 mL of 0.10M Hepes buffer, pH 7.5, containing 0.5M NaCl, 10% dimethylsulfoxide, and 0.020M MeO-Suc-AlaAlaPro-Val-p-nitroanilide as a substrate. Reactions were initiated by addition of 0.5 μg of elastase in 0.020 mL of 0.020M sodium acetate buffer, pH 6.0, and hydrolysis of substrate was monitored spectrophotometrically at 405 nm at 25° C. Assay results are set forth in Table 4, below, expressed as percentages of activity of control mixtures to which no inhibitor was added:

TABLE 4

| | Inhibition of Pancreatic Elastase | | |
|---|---|---|---|
| Inhibitor | Conc. (nM) | Time (min) | Activity % of Control |
| MeOSuc—Ala—Ala—Pro—Boroala—OH | 20 | 0.25 | 71.6 |
| | | 1.0 | 49.4 |
| | | 2.0 | 32.1 |
| | | 4.0 | 17.3 |
| MeOSuc—Ala—Ala—Pro—Boroval—OH | 50 | 0.5 | 74 |
| | | 2.0 | 44 |
| | | 4.0 | 28 |
| MeOSuc—Ala—Ala—Pro—Borophe—OH | 200 | 1.0$^a$ | 59 |
| MeOSuc—Ala—Ala—Pro—Boroala—pinacol | 200 | 0.25 | 61.7 |
| | | 2.0 | 24.7 |
| | | 4.0 | 2.5 |
| MeOSuc—Ala—Ala—Pro—Boroala—diethanolamine | 20 | 0.5 | 71.6 |
| | | 1.0 | 51.8 |
| | | 2.0 | 33.3 |
| | | 4.0 | 17.8 |
| Boc—Ala—Boroala diethanolamine | $5.0 \times 10^5$ | 1.0$^a$ | 67 |
| Boc—Phe—Pro—Borophe—pinacol | $5 \times 10^4$ | 0.5 | 69.1 |
| | | 4.0 | 21 |

$^a$Time dependency in inhibition was not observed during the assay.

Example 37: Titration of Pancreatic Elastase by MeOSuc-AlaAlaPro-Boroala-Diethanolamine Pancreatic elastase, obtained from commercial sources, was standardized by titration with varying concentrations of the above inhibitor. In these experiments, MeOSuc-AlaAlaPro-Boroala-diethanolamine was incubated with pancreatic elastase (1.25 μg), in 0.200 mL of 0.10M Hepes buffer, pH 7.5, containing 0.50M NaCl and 10% dimethylsulfoxide, for 5 minutes at room temperature. An aliquot (0.100 mL) was removed and assayed by the procedure described in Example 36, above.

Results are set forth in Table 5, below:

TABLE 5

| Titration of Pancreatic Elastase by MeOSuc—AlaAlaPro—Boroala—Diethanolamine | |
|---|---|
| Conc. of Inhibitor (nM) | % Activity |
| 0 | 100 |
| 25 | 80.6 |
| 50 | 61.8 |
| 75 | 42.6 |

TABLE 5-continued

| Titration of Pancreatic Elastase by MeOSuc—AlaAlaPro—Boroala—Diethanolamine | |
|---|---|
| Conc. of Inhibitor (nM) | % Activity |
| 100 | 34.4 |

The activity observed in mixtures without inhibitor was 0.0170 min$^{-1}$. A plot of % activity vs. concentration of 4 using 0-75 nM concentrations can be described by y = −0.765 nM$^{-1}$ × +100.2. The molar concentration of enzyme, determined from the intercept of the x-axis, is 130 nM. Using a molecular weight of 25,900 for elastase, the measured concentration of active enzyme is 3.37 μg/mL. The concentration of active enzyme initially used was 6.25 μg/mL, indicating an enzyme percentage activity of 54%. The manufacturer lists the preparation as 87% protein but does not specify the level of active enzyme present.

Example 38: Inhibition of Cathepsin G

A preparation of partially purified human Cathepsin G was obtained by the procedure of Baugh, et al., Biochemistry 15:836 (1976). Leukocytes were lysed and granules were isolated. The leukocyte granules were extracted with 0.20M sodium acetate, pH 4.0, and extracts were dialyzed against 0.05M Tris buffer, pH 8.0 containing 0.05M NaCl overnight at 4°. A protein fraction precipitated during dialysis and was isolated by centrifugation. This fraction contained most of the chymotrypsin-like activity of leukocyte granules.

Leukocyte granules are a major source for the preparation of leukocyte elastase and cathepsin G (chymotrypsin-like activity). Specific substrates have been prepared for each enzyme, namely MeOSuc-AlaAlaProVal-p-nitroanilide and Suc-AlaAlaPro-Phe-p-nitroanilide. The latter is not hydrolyzed by leukocyte elastase and is one of the better substrates for cathepsin G, according to Nakajima, et al., J. Biol. Chem. 254:4027 (1979), and accordingly, was used in the studies reported herein.

Enzyme preparations were assayed in 2.00 mL of 0.10M Hepes buffer, pH 7.5, containing 0.50M NaCl, 10% dimethylsulfoxide and 0.0020M Suc-AlaAlaPro-Phe-p-nitroanilide as a substrate. Hydrolysis of the p-nitroanilide substrate was monitored at 405 nm and at 25° C. Results are set forth in Table 6, below:

TABLE 6

| Inhibition of Cathepsin G (Leukocyte Chymotrypsin-Like Protease Preparation) | | |
|---|---|---|
| Inhibitor | Conc (M) | Activity % of Control$^a$ |
| MeOSuc—AlaAlaPro—Borophe—OH (Preparation A) | $2.0 \times 10^{-7}$ | 0$^b$ |
| | $2.0 \times 10^{-8}$ | 45$^b$ |
| MeOSuc—AlaAlaPro—Borophe—OH (Preparation B) | $2.0 \times 10^{-7}$ | 41$^b$ |
| MeOSuc—AlaAlaPro— | $1.0 \times 10^{-4}$ | 74 |

TABLE 6-continued

Inhibition of Cathepsin G (Leukocyte Chymotrypsin-Like Protease Preparation)

| Inhibitor | Conc (M) | Activity % of Control[a] |
|---|---|---|
| Boroval—OH | | |

[a]Control mixtures exhibit an activity of 0.0086 min$^{-1}$. No time dependence in inhibition was detected.
[b]Preparations A and B of this inhibitor are believed to reflect differences in degree of resolution of D and L diastereomers, resulting in differences in inhibitory capacity.

Example 39: Inhibition of α-Chymotrypsin

Bovine α-chymotrypsin, obtained from commercial sources, was used to prepare stock solutions. Assay mixtures contained, in a volume of 2.00 mL, 0.10M Hepes buffer, pH 7.5; 0.50M NaCl; 10% dimethylsulfoxide; $2.0 \times 10^{-4}$M Suc-AlaAlaPro-Phe-p-nitroanilide as substrate, and various concentrations of inhibitors. Reactions were initiated by the addition of 0.040 μg of enzyme and increases in absorbance were monitored spectrophotometrically at 405 nm at 25°. Results are set forth in Table 7, below:

TABLE 7

Inhibition of α-Chymotrypsin

| Inhibitor | Conc (nM) | Time (min) | Activity % of Control |
|---|---|---|---|
| MeOSuc—Ala—Ala—Pro—Borophe—OH (Preparation A) | 10 | 0.5 | 61 |
| | | 2 | 36 |
| | | 4 | 17 |
| MeOSuc—AlaAla—Pro—Boroala—OH | 50,000 | N.T[a] | 44 |
| MeOSuc—AlaAla—Pro—Boroval—OH | 25,000 | N.T | 55 |
| MeOSuc—AlaAla—Pro—Borophe—OH (Preparation B)[b] | 100 | N.T | 35 |
| Boc—Phe—Pro—Borophe—pinacol | 100 | N.T | 69 |

[a]N.T. No detectable time dependence in the degree of inhibition was observed during the 3-4 min assay time.
[b]Preparations A and B of this inhibitor are believed to reflect differences in degree of resolution of D and L diastereomers, thus accounting for differences in observed inhibitory capacity.

Example 40: Trituration of α-Chymotrypsin with MeOSuc-AlaAlaPro-Borophe-Diethanolamine In these experiments, α-chymotrypsin, obtained from commercial sources, was standardized by titration with various concentrations of MeOSuc-AlaAlaPro-Borophe-diethanolamine. In each case, enzyme was incubated with inhibitor for 5 minutes at 23°, in 0.01M Hepes buffer, pH 7.5, containing 0.50M NaCl and 10% dimethylsulfoxide. Aliquots were then removed and assayed for enzyme activity. Results are set forth in Tables 8 and 9, below:

TABLE 8

Titration of α-Chymotrypsin (3 μg/mL) by MeOSuc—AlaAla—Pro—Borophe—Diethanolamine in the 0-100 nM range

| Conc. of Inhibitor (nM) | % Activity |
|---|---|
| 0 | 100 |
| 25 | 68.2 |
| 50 | 52.3 |
| 75 | 31.8 |
| 100 | 18.2 |

As indicated in Table 7, assays were linear except for those measured at the 75 nM and 100 nM levels, in which slow activation was observed in assay cuvettes. A plot of activity versus inhibitor concentration for the remaining points is described by $y = -0.882$ nM$^{-1}$X + 96.15. The intercept on the x-axis is 109 nM. The measured level of active enzyme is 2.72 μg/mL, compared with the initial level of 3.0 μg/mL, indicating 91% purity by this criteria.

TABLE 9

Titration of α-Chymotrypsin (15 μg/mL) by MeOSuc—AlaAla—Pro—Borophe—Diethanolamine in the 0-500 nM range

| Conc. of Inhibitor (nM) | % Activity |
|---|---|
| 0 | 100 |
| 50 | 93.8 |
| 100 | 80.4 |
| 200 | 65.1 |
| 300 | 47.9 |
| 400 | 31.6 |
| 500 | 15.3 |

Activity of the control sample, above, was 0.0261 min$^{-1}$. All assays were linear, except for some slow activation observed at 500 nM and 400 nM levels of inhibitor. A plot of activity versus inhibitor concentration was linear level and is described by $y = -0.173$ nM$^{-1}$X + 100. The graph intercepted the x-axis at 578 nM. The level of active enzyme thus calculated using a molecular weight of 25,000 is 14.4 μg/mL (activity 96%).

Example 41: Inhibition of Pepsin

Pepsin activity was assayed by a procedure substantially similar to that described by Rich, et al., Biochem. Pharmac. 29:2205 (1980). Substrate, H-PheGlyHisPhe(-NO$_2$)PheAlaPhe-OCH$_3$,2 trifluoroacetate, and porcine pepsin were obtained from commercial sources.

Assay solutions, in a volume of 2.00 mL, contained $2.0 \times 10^{-4}$M substrate in 0.040M sodium formate buffer, pH 4.0, and 0.050 mL of inhibitor solutions in dimethylsulfoxide. Assays were initiated by addition of 0.020 mL of pepsin (0.10 mg/mL), and hydrolysis of substrate was monitored by measuring the increase in absorbance at 310 nm on a spectrophotometer. The results are set forth in Table 10, below:

TABLE 10

Inhibition of Pepsin (Acid Protease) by Peptides Containing an α-Aminoboronic Acid

| Inhibitor | Conc. (M) | % Activity[a] |
|---|---|---|
| Z—Phe—Gly—Ala—Boroleu—OH | $2.5 \times 10^{-4}$ | 58 |
|  | $5.0 \times 10^{-4}$ | 28 |
| Z—Phe—Gly—Ala—Boroleu—pinacol | $2.5 \times 10^{-4}$ | 58 |
|  | $5.0 \times 10^{-4}$ | 35 |
| Boc—Phe—Gly—Boroleu—pinacol | $5.0 \times 10^{-4}$ | 68 |
| Boc—Phe—Gly—Boroleu—diethanolamine | $5.0 \times 10^{-4}$ | 71 |
| H—Phe—Gly—Boroleu—pinacol | $5.0 \times 10^{-4}$ | 69 |
| MeOSuc—Ala—Ala—Pro—Boroval—OH | $5.0 \times 10^{-4}$ | 98 |
| MeOSuc—Ala—Ala—Pro—Borophe—OH | $5.0 \times 10^{-4}$ | 86 |
| Boc—Ala—Boroala—pinacol | $5.0 \times 10^{-4}$ | 90 |
| Boc—Ala—Boroala—diethanolamine | $5.0 \times 10^{-4}$ | 85 |
| Boc—Gly—Boroleu— | $5.0 \times 10^{-4}$ | 87 |

TABLE 10-continued

| Inhibition of Pepsin (Acid Protease) by Peptides Containing an α-Aminoboronic Acid | | |
|---|---|---|
| Inhibitor | Conc. (M) | % Activity[a] |
| pinacol Boc—Gly—Boroleu— diethanolamine | 5.0 × 10$^{-4}$ | 90 |

[a]The activity of the control was 0.0027 min$^{-1}$.

Example 42: Inhibition of Thermolysin

The metalloenzyme thermolysin was assayed by a procedure substantially similar to that described by Feder et al., Biochemistry 9:2784 (1970). Substrate, furylacryloyl-glycyl-leucinamide, and thermolysin were obtained from commercial sources. Assay solutions consisted of furylacryloyl-glycyl-leucinamide (0.100 mL, 8.0×10$^{-3}$M in N,N-dimethylformamide) and 1.90 mL of 0.50M Tris buffer, pH 7.5, containing 0.10M NaCl and 0.010M CaCl$_2$. Either 0.100 mL of dimethylsulfoxide or 0.100 mL of dimethylsulfoxide containing inhibitor was added and the reaction was initiated by the addition of 0.020 mL of thermolysin (1.0 mg/mL). The rate of hydrolysis was monitored by measuring the decrease in absorbance at 345 nm. Results are set forth in Table 11, below:

TABLE 11

| Inhibition of Thermolysin (Metallo Protease) by Peptides Containing α-Aminoboronic Acids | | |
|---|---|---|
| Inhibitor | Conc. (M) | % Activity[a] |
| Z—Phe—Gly—Ala— Boroleu—OH | 2.5 × 10$^{-4}$ 5.0 × 10$^{-4}$ | 75 60 |
| Z—Phe—Gly—Ala— Boroleu—pinacol | 2.5 × 10$^{-4}$ 5.0 × 10$^{-4}$ | 76 66 |
| MeOSuc—Ala—Ala— Pro—Borophe—OH (Preparation A)[b] | 2.5 × 10$^{-4}$ | 58 |
| MeOSuc—Ala—Ala— Pro—Borophe—OH (Preparation B)[b] | 2.5 × 10$^{-4}$ 5.0 × 10$^{-4}$ | 101 90 |
| MeOSuc—Ala—Ala— Pro—Borophe—pinacol | 5.0 × 10$^{-4}$ | 76 |
| MeOSuc—Ala—Ala— Pro—Boroval—OH | 5.0 × 10$^{-4}$ | 82 |
| Boc—Ala—Boroala— pinacol | 5.0 × 10$^{-4}$ | 102 |
| Boc—Ala—Boroala— diethanolamine | 5.0 × 10$^{-4}$ | 99 |

[a]The activity of the control ([Inhibitor] = 0) was 0.007625 min$^{-1}$.
[b]Preparations A and B are believed to reflect differences in the degree of resolution of D and L diastereomers, thus accounting for differences in inhibitory capacity.

Example 43: Determination of Plasma Inhibitor Concentrations

Standardized pancreatic elastase was employed to titrate plasma samples containing MeOSu-AlaAlaPro-Boroval-OH by procedures substantially similar to those detailed in Example 37, above, for MeOSu-AlaAlaPro-Boroala-OH. Plasma, 5 μL, containing various concentrations of inhibitor, or a dilution thereof, was incubated with 10 μL of a stock solution of 1.15×10$^{-5}$M pancreatic elastase, in a final volume of 0.40 mL 0.10M Hepes buffer, pH 7.5, containing 0.5M NaCl at 25°. After 5 minutes incubation, 1.60 mL additional buffer and 20 μL of a 0.20M MeOSuc-AlaAla-Pro-Val-pNA solution in dimethylsulfoxide was added and the increase in absorbance at 405 nm monitored. Levels of inhibitor were determined from a standard curve of % activity vs. inhibitor concentration.

The standard curve was prepared by enzyme assays conducted using samples containing various concentrations of inhibitor in normal saline. A similar standard curve was prepared by incubating varying concentrations of inhibitor in hamster plasma to establish the validity of the assay. The results of these experiments are set forth in Table 12, below:

TABLE 12

| Standard Curves for Determination of MeOSuc—AlaAlaPro—Boroval—OH in Plasma | | |
|---|---|---|
| Conc. of Inhibitor (μM) | Activity in Saline (% of Control) | Activity in Plasma (% of Control) |
| 0 | 100 | 65 |
| 10 | 85 | 49 |
| 20 | 67 | 32 |
| 40 | 45 | 17 |
| 80 | 13 | — |

For the samples containing inhibitor in saline, a plot of activity vs. concentration was linear for the range of 0–20 μM, and is described by the line y=−1.65 μM$^{-1}$x+100.5. The x intercept thus determined was 60.9 μM. For a 1:1 complex of inhibitor and enzyme a value of 23 μM is predicted. This deviation is believed to be due to the fact that the inhibitor employed was an unresolved mixture of diastereomers.

For samples containing inhibitor in plasma, a plot of activity vs. concentration was linear for the range of 0–20 μM, and is described by the line y=−1.65 μM$^{-1}$x+65.2. The approximate 35% inhibition observed in plasma samples containing no inhibitor is attributable to plasma elastase inhibitors and is referred to as normal elastase inhibitory capacity (EIC).

The stability of inhibitory capacity provided by MeOSuc-AlaAlaPro-Boroval-OH in plasma was determined by incubating samples of plasma containing inhibitor at 4° for 24 hours, followed by assays for inhibitory capacity conducted as above. In a related experiment, MeOSu-AlaAlaPro-Boroval-pinacol was incubated with plasma samples for 24 hours at 23°, with no detectable loss of inhibitory capacity. It should be noted that the pinacol-protected form of the foregoing compound is hydrolyzed to the free acid within 20 minutes in plasma. The results of the experiments involving MeOSuc-AlaAlaPro-Boroval-OH are set forth in Table 13, below:

TABLE 13

| Stability of Inhibitory Capacity of MeOSuc—AlaAlaPro—Boroval—OH in Plasma | | |
|---|---|---|
| | % Activity | |
| | t = 0 hr. | t = 48 hr. |
| Control | 100 | 100 |
| Plasma | 63 | 65 |
| Plasma + Inhibitor | 18.5 | 17 |

Figure 1:
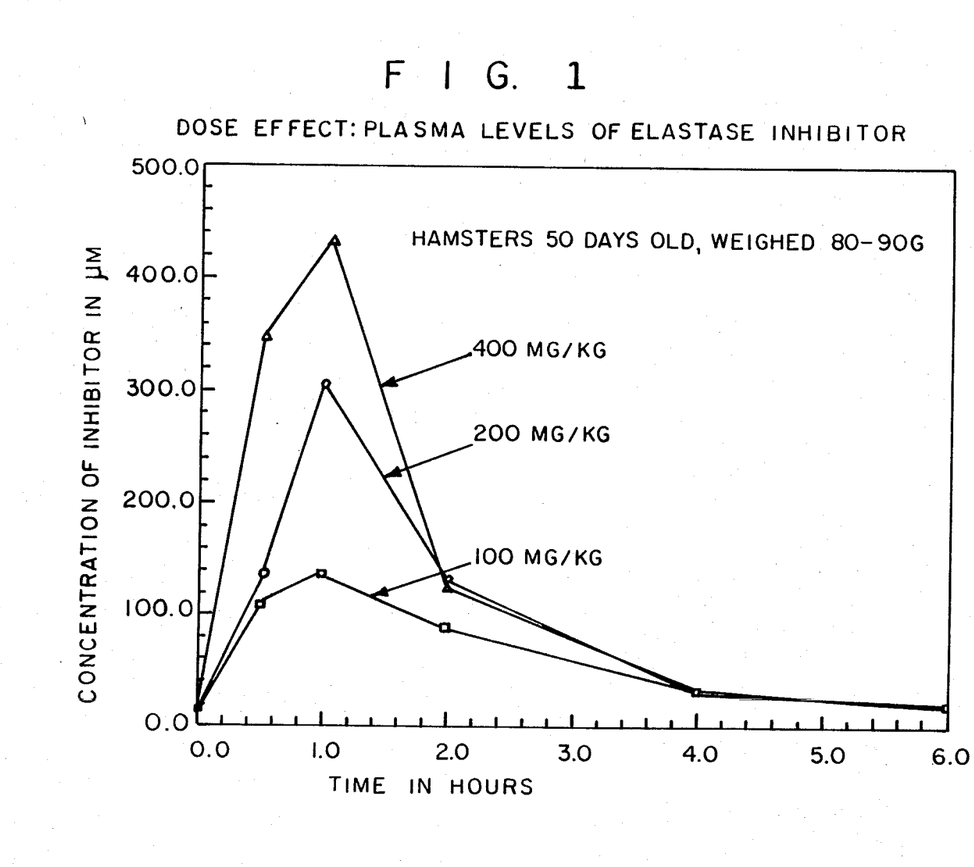
FIG. 1 illustrates plasma levels of elastase inhibitory capacity in hamsters at various times following intraperitoneal administration of MeOSuc-AlaAlaPro-Boroval-pinacol at 100, 200 and 400 mg/kg dosage levels.

FIG. 1 illustrates results of experiments in which hamsters, 50 days old, weighing 80–90 g, were administered MeOSu-AlaAlaPro-Boroval-pinacol in 1.0 mL saline at intraperitoneal dosage levels of 400, 200 and 100 mg/kg. At the indicated time intervals, blood samples (50–100 μL) were withdrawn by cardiac puncture from animals lightly anesthetized with ether, and elastase inhibitor levels determined. Normal plasma EIC is 14 μM. As indicated in FIG. 1, a 200 mg/kg dose elevated plasma EIC approximately 20-fold after one hour. In other experiments, variations in the level of plasma EIC elevation have been observed, but in each case, at least 10-fold elevation was attained. Subcutaneous administration of this compound at 130-150 mg/kg resulted in an approximate 10-fold elevation in EIC after one hour which decreased to about 4-fold after 2 hours. For intramuscular injection at 200 mg/kg, a 10-fold elevation in EIC was observed after 30 minutes, which decreased to 6-fold after one hour.

Figure 2:
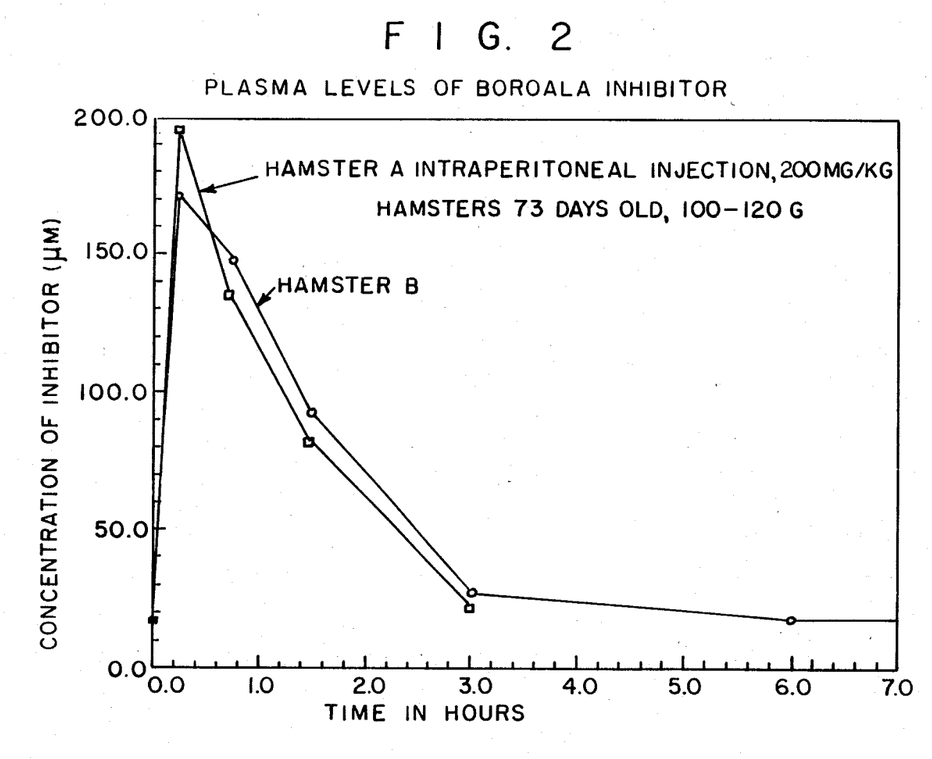
FIG. 2 illustrates plasma levels of elastase inhibitory capacity in hamsters at various times following intraperitoneal administration of MeOSuc-AlaAlaPro-Boroala-pinacol at 200 mg/kg.

FIG. 2 illustrates results of a related series of experiments, in which hamsters 73 days old, weighing 100-120 g were administered MeOSuc-AlaAlaPro-Boroala-pinacol at a dosage level of 200 mg/kg. Plasma samples were withdrawn at various time intervals and assayed for inhibitory capacity as described previously, extent that the inhibitor employed in construction of a standard curve was incubated in 0.10M sodium phosphate buffer, pH 7.5, for one hour prior to assay to convert the pinacol derivative to the free form. The line describing the standard curve is $y = -2.29 \mu M^{-1} x + 104$. Levels of inhibitory capacity were determined by reference to the linear region (0-20 $\mu$M inhibitor) of the standard curve. Results are depicted in FIG. 2.

Figure 3:
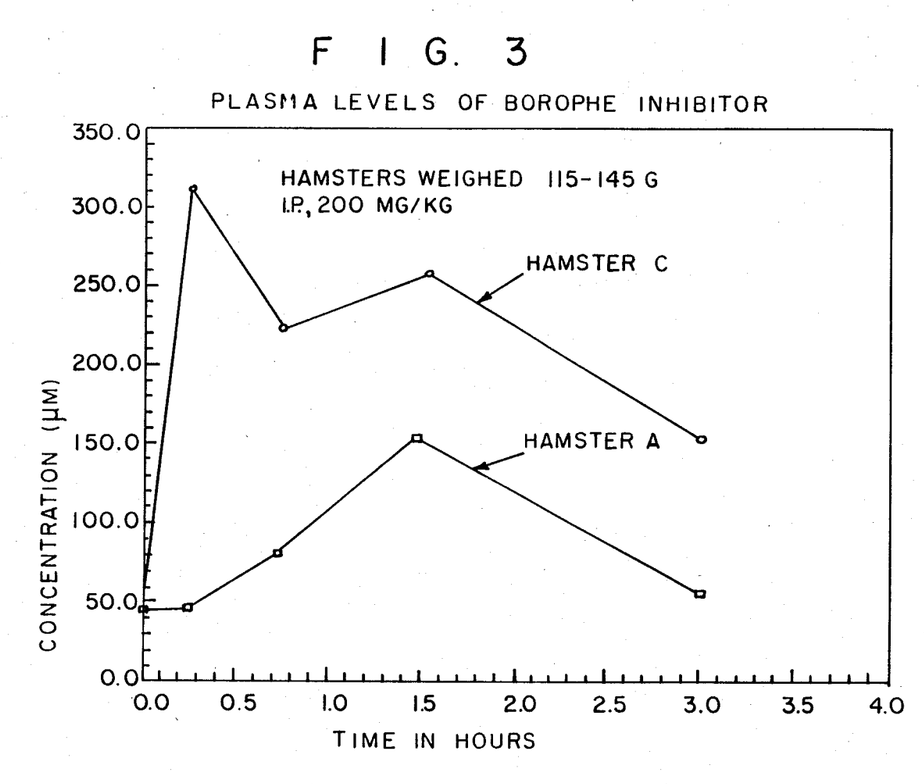
FIG. 3 illustrates plasma levels of MeOSuc-AlaAla-Pro-Borophe-pinacol in hamsters following intraperitoneal administration at 200 mg/kg.

FIG. 3 depicts the results of experiments in which plasma levels of MeOSuc-AlaAlaPro-Borophe-pinacol were determined at various times following administration to hamsters weighing 110-125 g, at a dosage level of 200 mg/kg. Plasma levels were determined by a procedure similar to that described for FIG. 2, above, except chymotrypsin was employed in the assay. Plasma or an appropriate dilution (5 $\mu$L) was added to a solution consisting of 175 $\mu$L 0.10M Hepes buffer, pH 7.5, containing 0.50M NaCl and 30 $\mu$L chymotrypsin (4.0 $\mu$M) in 1.0 mM HCl. After incubation for 5 minutes at about 23°, a 40 $\mu$L aliquot was assayed by the procedure described previously for chymotrypsin (Example 39). Plasma concentrations of the test compound were determined from a standard curve of percent activity vs. concentration of MeOSuc-AlaAlaPro-Borophe-pinacol in a 5 $\mu$L sample. As previously described for MeOSuc-AlaAlaPro-Boroala-pinacol, the standard curve was prepared by first incubating the inhibitor, in pinacol form, in 0.10M sodium phosphate buffer, pH 7.5. The standard curve is described by the line $y = -1.99 \mu M^{-1} x + 96.2$, and the region from 0-25 $\mu$M was used to determine plasma concentrations.

Toxicity Studies

To evaluate the potential for CNS toxicity of the compounds of the invention, male CF$_1$ mice were fasted overnight and then administered MeOSuc-AlaAlaPro-Boroval-pinacol in saline, intravenously at dosage levels of 180 mg/kg, 90 mg/kg, 45 mg/kg, and 0 mg/kg. Five mice were included in each dosage group. The test mice were observed continuously for 90 minutes following administration of the test compound, and again at 18 and 24 hours after administration. No mortality, behavioral changes, or other symptoms of acute toxicity were observed during the test period.

What is claimed is:

1. A compound of the formula or a physiologically acceptable salt thereof, wherein $A^1$ is an amino acid of L-configuration selected from the group consisting of Ala, Pro, Gly, Glu, Leu, Lys, Phe, Ser, Val, Ile, Arg, Tyr, Thr, Asp, Asn or Gln;

$A^2$ and $A^3$ are, independently, amino acids of D or L-configuration selected from the group consisting of Ala, Arg, Asn, Asp, Cys, Gln, Glu, Gly, His, Ile, Leu, Lys, Met, Phe, Pro, Ser, Thr, Trp, Tyr or Val;

n is 1 and o is 0 or 1;

$R^1$ is —H or an N-terminal protecting group;

$R^2$ is an alkyl group of one to six carbons, optionally comprising an aromatic substituent, or one or more in-chain bivalent groups selected from the group consisting of —O—, —CO—, —S—, —NH—, —CONH—, —CH=CH— or —SO$_2$—; and $Y^1$ and $Y^2$ are each —H, or taken together form a moiety derived from a dihydroxy compound having at least two hydroxy groups separated by at least two connecting atoms in a chain or ring, said chain or ring comprising carbon atoms, and optionally, a heteroatom or heteroatoms which can be N, S, or O; with the proviso that where is O, $R^1$ cannot be —H.

2. A compound according to claim 1 wherein $A^1$ is Ala, Pro, Gly, Glu, Leu, Lys, Phe or Ser; and o is 1.

3. A compound according to claim 2 wherein $R^2$ is

—CH$_3$, —CH(CH$_3$)$_2$, —CH$_2$CH(CH$_3$)$_2$, —CH(CH$_3$)CH$_2$CH$_3$ or

4. A compound according to claim 3 wherein $R^1$ is MeOSuc, Suc, Boc, Z, Ac or Bz.

5. A compound according to claim 4 wherein $Y^1$ and $Y^2$ are each —H, or a moiety derived from pinacol or diethanolamine.

6. A compound according to claim 5 wherein $A^1$ is Pro, Ala, Leu, Lys, Gly or Ser.

7. A compound according to claim 6 wherein $A^2$ and $A^3$ are, independently, Ala, Pro, Gly, Phe, or Lys.

8. A compound according to claim 7 wherein $A^1$ is Pro; and $A^2$ and $A^3$ are each Ala.

9. A compound according to claim 8 wherein $R^2$ is —CH(CH$_3$)$_2$.

10. A compound according to claim 8 wherein $R^2$ is —CH$_3$.

11. A compound according to claim 8 wherein $R^2$ is —CH$_2$CH(CH$_3$)$_2$.

12. A compound according to claim 8 wherein $R^2$ is —CH(CH$_3$)CH$_2$CH$_3$.

13. A compound according to claim 8 wherein $R^2$ is

14. A compound according to claim 9 wherein $R^1$ is MeOSuc.

15. A compound according to claim 14 wherein $Y^1$ and $Y^2$ are each —H.

16. A composition for inhibiting proteolysis in a mammal, comprising an amount of a compound of claim 1 effective to inhibit proteolysis, and a physiologically acceptable carrier or diluent.

17. A composition for inhibiting proteolysis in a mammal, comprising an amount of a compound of claim 3 effective to inhibit proteolysis, and a physiologically acceptable carrier or diluent.

18. A method of inhibiting proteolysis in a mammal, comprising administering to the mammal a composition of claim 16.

19. A method of inhibiting proteolysis in a mammal, comprising administering to the mammal a composition of claim 17.

* * * * *